US008652511B2

(12) United States Patent
Cottrell et al.

(10) Patent No.: US 8,652,511 B2
(45) Date of Patent: Feb. 18, 2014

(54) TRANSDERMAL DELIVERY PATCH

(75) Inventors: Jeremy Cottrell, Caulfield South (AU); Giacinto Gaetano, South Melbourne (AU); Mahmoud El-Tamimy, Meadow Heights (AU); Nicholas Kennedy, Boronia (AU); Paul David Gavin, Chadstone (AU)

(73) Assignee: Phosphagenics Limited, Clayton, Victoria (AU)

( * ) Notice: Subject to any disclaimer, the term of this patent is extended or adjusted under 35 U.S.C. 154(b) by 0 days.

(21) Appl. No.: 13/501,500

(22) PCT Filed: Mar. 30, 2011

(86) PCT No.: PCT/AU2011/000358
§ 371 (c)(1),
(2), (4) Date: Apr. 12, 2012

(87) PCT Pub. No.: WO2011/120084
PCT Pub. Date: Oct. 6, 2011

(65) Prior Publication Data
US 2012/0201891 A1 Aug. 9, 2012

Related U.S. Application Data

(60) Provisional application No. 61/319,002, filed on Mar. 30, 2010, provisional application No. 61/319,007, filed on Mar. 30, 2010.

(51) Int. Cl.
*A61F 13/00* (2006.01)
(52) U.S. Cl.
USPC ........................................... 424/449; 424/443
(58) Field of Classification Search
None
See application file for complete search history.

(56) References Cited

U.S. PATENT DOCUMENTS

| | | | |
|---|---|---|---|
| 2,407,823 A | 9/1946 | Fieser | |
| 2,667,479 A | 1/1954 | Hoffman et al. | |
| 2,913,477 A | 11/1959 | Hirschmann | |
| 3,127,434 A | 3/1964 | Andrews | |
| 3,212,901 A | 10/1965 | Robeson | |
| 3,607,765 A | 9/1971 | Wixon | |
| 4,075,333 A | 2/1978 | Josse | |
| 4,141,938 A | 2/1979 | Klose | |
| 4,299,906 A | 11/1981 | Liu | |
| 4,369,172 A | 1/1983 | Schor et al. | |
| 4,444,755 A | 4/1984 | Horrobin | |
| 4,603,142 A | 7/1986 | Burger et al. | |
| 4,654,373 A | 3/1987 | Bertelli | |
| 4,684,520 A | 8/1987 | Bertelli | |
| 4,686,211 A | 8/1987 | Hara et al. | |
| 4,874,883 A | 10/1989 | Uphues et al. | |
| 4,952,495 A | 8/1990 | Belly et al. | |
| 4,977,282 A | 12/1990 | Baldwin et al. | |
| 5,041,434 A | 8/1991 | Lubkin | |
| 5,053,222 A | 10/1991 | Takasu et al. | |
| 5,091,848 A | 2/1992 | Kojima | |
| 5,094,848 A | 3/1992 | Brixner | |
| 5,114,957 A | 5/1992 | Hendler et al. | |
| 5,138,084 A | 8/1992 | Casagrande et al. | |
| 5,173,304 A | 12/1992 | Lohner et al. | |
| 5,334,378 A | 8/1994 | Mitani et al. | |
| 5,374,645 A | 12/1994 | Kurihara-Bergstrom et al. | |
| 5,387,579 A | 2/1995 | Meybeck et al. | |
| 5,446,070 A | 8/1995 | Mantelle | |
| 5,474,891 A | 12/1995 | Murphy | |
| 5,474,991 A | 12/1995 | Ogata et al. | |
| 5,554,781 A | 9/1996 | Reierson | |
| 5,570,504 A | 11/1996 | Distefano et al. | |
| 5,583,105 A | 12/1996 | Kovacs et al. | |
| 5,589,504 A | 12/1996 | Dannenberg et al. | |
| 5,603,949 A | 2/1997 | Meybeck et al. | |
| 5,607,921 A | 3/1997 | Bernard et al. | |
| 5,643,597 A | 7/1997 | Meybeck et al. | |
| 5,656,618 A | 8/1997 | Meybeck et al. | |
| 5,656,672 A | 8/1997 | Collin et al. | |
| 5,741,518 A | 4/1998 | Ribier et al. | |
| 5,759,526 A | 6/1998 | Simonnet et al. | |
| 5,776,915 A | 7/1998 | Peterson et al. | |
| 5,780,504 A | 7/1998 | Ptchelintsev | |
| 5,804,168 A | 9/1998 | Murad | |
| 5,804,216 A | 9/1998 | Terren et al. | |
| 5,807,542 A | 9/1998 | Challis et al. | |
| 5,807,845 A | 9/1998 | Ogata et al. | |
| 5,885,595 A | 3/1999 | Corey et al. | |
| 5,906,811 A | 5/1999 | Hersh | |

(Continued)

FOREIGN PATENT DOCUMENTS

| | | |
|---|---|---|
| CA | 1337992 | 1/1996 |
| CA | 2426852 | 5/2002 |

(Continued)

OTHER PUBLICATIONS

Gianello et al. Subchronic Oral Toxicity Study of Mixed Tocopheryl Phosphates in Rates, International Journal of Toxicology, 26;475-490; 2007.*
Biotech Daily, "Phosphagenics Insulin Patch 'On Track for 2010 Trials,'" Dec. 17, 2009 (7 pages).
Biotech Daily, "Phosphagenics Phospha-E Fails Nestle Metabolic Trial," Dec. 15, 2009 (6 pages).
Biotech Daily, "Phosphagenics Transdermal Oxycodone Patch 'Success,'" Feb. 1, 2010 (7 pages).
Phosphagenics Limited Newsletter, Mar. 2010 (4 pages).
Phosphagenics Limited Newsletter, Sep. 2009 (6 pages).
Phosphagenics Limited, "TPM/Oxycodone Fact Sheet," Apr. 2010 (1 page).
Phosphagenics Limited, Annual General Meeting—Chairman Address and AGM Presentation "Delivering Topically and Systemically," May 29, 2009 (32 pages).

(Continued)

*Primary Examiner* — Anand Desai
*Assistant Examiner* — Melissa Mercier
(74) *Attorney, Agent, or Firm* — Michael Best & Friedrich LLP

(57) ABSTRACT

A composition suitable for use in a transdermal delivery patch for administration of a biologically active compound, the composition comprising a phosphate compound of tocopherol and a polymer carrier.

44 Claims, 13 Drawing Sheets

(56) References Cited

U.S. PATENT DOCUMENTS

| | | |
|---|---|---|
| 5,908,846 A | 6/1999 | Bundgaard et al. |
| 5,916,915 A | 6/1999 | Hong et al. |
| 5,928,631 A | 7/1999 | Lucas et al. |
| 5,952,361 A | 9/1999 | Dias Nahoum |
| 5,952,373 A | 9/1999 | Lanzendorfer et al. |
| 5,965,750 A | 10/1999 | Oonishi et al. |
| 5,981,474 A | 11/1999 | Manning et al. |
| 5,985,856 A | 11/1999 | Stella et al. |
| 6,022,867 A | 2/2000 | Ito et al. |
| 6,028,105 A | 2/2000 | Nigra |
| 6,046,181 A | 4/2000 | Oonishi et al. |
| 6,048,891 A | 4/2000 | Wechter |
| 6,096,326 A | 8/2000 | Wikholm |
| 6,121,249 A | 9/2000 | Weissman et al. |
| 6,143,770 A | 11/2000 | Lane et al. |
| 6,184,247 B1 | 2/2001 | Schneider |
| 6,231,885 B1 | 5/2001 | Carrara |
| 6,248,758 B1 | 6/2001 | Klokkers et al. |
| 6,248,779 B1 | 6/2001 | Shimizu et al. |
| 6,361,800 B1 | 3/2002 | Cooper et al. |
| 6,384,043 B1 | 5/2002 | Peyman et al. |
| 6,403,811 B1 | 6/2002 | West |
| 6,417,223 B1 | 7/2002 | Sanders et al. |
| 6,423,742 B1 | 7/2002 | Larson |
| 6,444,220 B2 | 9/2002 | Wiley |
| 6,444,234 B1 | 9/2002 | Kirby et al. |
| 6,479,540 B1 | 11/2002 | Constantinides et al. |
| 6,485,950 B1 | 11/2002 | Kumar et al. |
| 6,503,545 B1 | 1/2003 | Perlman et al. |
| 6,579,995 B1 | 6/2003 | West |
| 6,599,933 B2 | 7/2003 | Takada et al. |
| 6,641,847 B1 | 11/2003 | Nawar |
| 6,645,998 B2 | 11/2003 | Sanders et al. |
| 6,703,384 B2 | 3/2004 | Sanders et al. |
| 6,727,280 B2 | 4/2004 | Paiepu et al. |
| 6,770,672 B1 | 8/2004 | Sanders et al. |
| 6,887,648 B2 | 5/2005 | Pavelchek et al. |
| 7,074,825 B2 | 7/2006 | Mo et al. |
| 7,179,486 B1 | 2/2007 | Mulye |
| 7,648,710 B2 | 1/2010 | West |
| 8,008,345 B2 | 8/2011 | West et al. |
| 2001/0006659 A1 | 7/2001 | Koike et al. |
| 2001/0044462 A1 | 11/2001 | Hensley et al. |
| 2002/0045765 A1 | 4/2002 | Kim et al. |
| 2002/0127198 A1 | 9/2002 | Rothbard et al. |
| 2002/0131994 A1 | 9/2002 | Schur et al. |
| 2002/0132845 A1 | 9/2002 | Miller et al. |
| 2002/0151467 A1 | 10/2002 | Leung |
| 2003/0035812 A1 | 2/2003 | Ito et al. |
| 2003/0109575 A1 | 6/2003 | Lambert et al. |
| 2003/0157326 A1 | 8/2003 | Vaghefi et al. |
| 2003/0206972 A1 | 11/2003 | Babish et al. |
| 2003/0220301 A1 | 11/2003 | Lal et al. |
| 2004/0052754 A1 | 3/2004 | West et al. |
| 2004/0067890 A1 | 4/2004 | Gupta |
| 2004/0097431 A1 | 5/2004 | Sanders et al. |
| 2004/0097472 A1 | 5/2004 | West et al. |
| 2004/0131569 A1 | 7/2004 | Schneider et al. |
| 2004/0167081 A1 | 8/2004 | Abbruzzese et al. |
| 2004/0204343 A1 | 10/2004 | Fishman |
| 2004/0234602 A1 | 11/2004 | Fischer et al. |
| 2004/0235938 A1 | 11/2004 | Sanders et al. |
| 2004/0241225 A1 | 12/2004 | West et al. |
| 2005/0009787 A1 | 1/2005 | West et al. |
| 2005/0089495 A1 | 4/2005 | West et al. |
| 2005/0134664 A1 | 6/2005 | Pavlin |
| 2005/0220733 A1 | 10/2005 | Tsuzuki et al. |
| 2006/0120979 A1 | 6/2006 | Rubin |
| 2006/0228395 A1 | 10/2006 | Lamb et al. |
| 2006/0241085 A1 | 10/2006 | West et al. |
| 2006/0257459 A1 | 11/2006 | West et al. |
| 2006/0281715 A1 | 12/2006 | West |
| 2006/0281716 A1 | 12/2006 | West et al. |
| 2007/0042999 A1 | 2/2007 | West et al. |
| 2007/0135390 A1 | 6/2007 | West et al. |
| 2007/0141133 A1 | 6/2007 | Wang et al. |
| 2007/0224253 A1 | 9/2007 | Franklin |
| 2008/0233178 A1 | 9/2008 | Reidenberg et al. |
| 2008/0254073 A1 | 10/2008 | Chi |
| 2009/0004166 A1 | 1/2009 | West et al. |
| 2009/0005348 A1 | 1/2009 | Ogru et al. |
| 2009/0036354 A1 | 2/2009 | Gavin et al. |
| 2009/0104258 A1 | 4/2009 | Dumas et al. |
| 2009/0186856 A1 | 7/2009 | West et al. |
| 2009/0233881 A1 | 9/2009 | West et al. |
| 2009/0239827 A1 | 9/2009 | Ogru et al. |
| 2009/0274677 A1 | 11/2009 | Isaacs et al. |
| 2010/0076094 A1 | 3/2010 | West |
| 2010/0209459 A1 | 8/2010 | West et al. |
| 2010/0222305 A1 | 9/2010 | West et al. |
| 2010/0261670 A1 | 10/2010 | West et al. |
| 2011/0003774 A1 | 1/2011 | West et al. |

FOREIGN PATENT DOCUMENTS

| | | |
|---|---|---|
| CA | 2426885 | 5/2002 |
| EP | 0171009 | 2/1986 |
| EP | 0324387 | 7/1989 |
| EP | 0338429 | 10/1989 |
| EP | 0430045 | 6/1991 |
| EP | 0430336 | 6/1991 |
| EP | 0436911 | 7/1991 |
| EP | 0565007 | 10/1993 |
| EP | 0574255 | 12/1993 |
| EP | 0612521 | 8/1994 |
| EP | 0617963 | 10/1994 |
| EP | 0641790 | 3/1995 |
| EP | 0643969 | 3/1995 |
| EP | 0661053 | 7/1995 |
| EP | 0669132 | 8/1995 |
| EP | 0669437 | 8/1995 |
| EP | 0674904 | 10/1995 |
| EP | 0679399 | 11/1995 |
| EP | 0680760 | 11/1995 |
| EP | 0681840 | 11/1995 |
| EP | 0684043 | 12/1995 |
| EP | 0699440 | 3/1996 |
| EP | 0826365 | 3/1998 |
| EP | 0845216 | 6/1998 |
| EP | 0699437 | 12/1998 |
| EP | 0965328 | 12/1999 |
| EP | 1000541 | 5/2000 |
| EP | 1023897 | 8/2000 |
| EP | 1053749 | 11/2000 |
| EP | 1264595 | 12/2002 |
| EP | 1470817 | 10/2004 |
| EP | 1783209 | 5/2007 |
| FR | 2777179 | 10/1999 |
| GB | 778142 | 7/1957 |
| GB | 1121683 | 7/1968 |
| GB | 2227662 | 8/1990 |
| JP | 50022535 | 3/1975 |
| JP | 52039013 | 3/1977 |
| JP | 53015381 | 2/1978 |
| JP | 58180410 | 10/1983 |
| JP | 59044375 | 3/1984 |
| JP | 59157091 | 9/1984 |
| JP | 60197621 | 10/1985 |
| JP | 61086940 | 5/1986 |
| JP | 61091137 | 5/1986 |
| JP | 61176535 | 8/1986 |
| JP | 61233631 | 10/1986 |
| JP | 62195393 | 8/1987 |
| JP | 63093791 | 4/1988 |
| JP | 63139972 | 6/1988 |
| JP | 1228920 | 9/1989 |
| JP | 1274830 | 11/1989 |
| JP | 03-072426 | 3/1991 |
| JP | 03-120230 | 5/1991 |
| JP | 4208209 | 7/1992 |
| JP | 4270212 | 9/1992 |
| JP | 05-000946 | 1/1993 |
| JP | 5132700 | 5/1993 |
| JP | 5201858 | 8/1993 |

(56) References Cited

FOREIGN PATENT DOCUMENTS

| | | |
|---|---|---|
| JP | 6048962 | 2/1994 |
| JP | 6056699 | 3/1994 |
| JP | 6078214 | 10/1994 |
| JP | 7011291 | 1/1995 |
| JP | 7207298 | 8/1995 |
| JP | 7278587 | 10/1995 |
| JP | 7316170 | 12/1995 |
| JP | 8073338 | 3/1996 |
| JP | 8193089 | 7/1996 |
| JP | 08-231564 | 9/1996 |
| JP | 8311085 | 11/1996 |
| JP | 8311489 | 11/1996 |
| JP | 8325594 | 12/1996 |
| JP | 9044375 | 2/1997 |
| JP | 9309813 | 12/1997 |
| JP | 10045783 | 2/1998 |
| JP | 10155429 | 6/1998 |
| JP | 10509451 | 9/1998 |
| JP | 10511677 | 11/1998 |
| JP | 11043436 | 2/1999 |
| JP | 11506419 | 6/1999 |
| JP | 11199424 | 7/1999 |
| JP | 11199465 | 7/1999 |
| JP | 2000198701 | 7/2000 |
| JP | 2001169731 | 6/2001 |
| JP | 2001247585 | 9/2001 |
| JP | 2002080475 | 3/2002 |
| JP | 2002088091 | 3/2002 |
| JP | 2003128531 | 5/2003 |
| JP | 2003171313 | 6/2003 |
| NZ | 244549 | 7/1994 |
| SU | 925961 | 5/1982 |
| WO | WO 91/17987 | 11/1991 |
| WO | WO 92/03122 | 3/1992 |
| WO | WO 92/07544 | 5/1992 |
| WO | WO 92/08459 | 5/1992 |
| WO | WO 92/15289 | 9/1992 |
| WO | WO 93/02661 | 2/1993 |
| WO | WO 93/09768 | 5/1993 |
| WO | WO 93/15731 | 8/1993 |
| WO | WO 93/24131 | 12/1993 |
| WO | WO 95/31217 | 11/1995 |
| WO | WO 95/34303 | 12/1995 |
| WO | WO 96/17852 | 6/1996 |
| WO | WO 96/20715 | 7/1996 |
| WO | WO 96/21440 | 7/1996 |
| WO | WO 96/29336 | 9/1996 |
| WO | WO 96/37196 | 11/1996 |
| WO | WO 97/02803 | 1/1997 |
| WO | WO 97/14705 | 4/1997 |
| WO | WO 97/35591 | 10/1997 |
| WO | WO 99/35242 | 7/1999 |
| WO | WO 99/58555 | 11/1999 |
| WO | WO 00/08033 | 2/2000 |
| WO | WO 00/16772 | 3/2000 |
| WO | WO 00/30620 | 6/2000 |
| WO | WO 00/43380 | 7/2000 |
| WO | WO 00/44237 | 8/2000 |
| WO | WO 00/44375 | 8/2000 |
| WO | WO 00/53728 | 9/2000 |
| WO | WO 00/57876 | 10/2000 |
| WO | WO 00/59475 | 10/2000 |
| WO | WO 00/69865 | 11/2000 |
| WO | WO 00/71094 | 11/2000 |
| WO | WO 00/71125 | 11/2000 |
| WO | WO 00/74684 | 12/2000 |
| WO | WO 01/13901 | 3/2001 |
| WO | WO 01/19372 | 3/2001 |
| WO | WO 01/22937 | 4/2001 |
| WO | WO 01/35998 | 5/2001 |
| WO | WO 01/46204 | 6/2001 |
| WO | WO 01/54674 | 8/2001 |
| WO | WO 01/58889 | 8/2001 |
| WO | WO 0154674 A1 * | 8/2001 |
| WO | WO 01/72300 | 10/2001 |
| WO | WO 02/13810 | 2/2002 |
| WO | WO 02/26238 | 4/2002 |
| WO | WO 02/36736 | 5/2002 |
| WO | WO 02/39996 | 5/2002 |
| WO | WO 02/40033 | 5/2002 |
| WO | WO 02/40034 | 5/2002 |
| WO | WO 03/011303 | 2/2003 |
| WO | WO 03/013550 | 2/2003 |
| WO | WO 03/024429 | 3/2003 |
| WO | WO 03/024430 | 3/2003 |
| WO | WO 03/026673 | 4/2003 |
| WO | WO 03/039461 | 5/2003 |
| WO | WO 03/043570 | 5/2003 |
| WO | WO 03/049774 | 6/2003 |
| WO | WO 03/053407 | 7/2003 |
| WO | WO 03/068209 | 8/2003 |
| WO | WO 03/097714 | 11/2003 |
| WO | WO 03/101480 | 12/2003 |
| WO | WO 2004/014432 | 2/2004 |
| WO | WO 2004/060315 | 7/2004 |
| WO | WO 2004/064831 | 8/2004 |
| WO | WO 2004/091636 | 10/2004 |
| WO | WO 2004/092186 | 10/2004 |
| WO | WO 2004/092187 | 10/2004 |
| WO | WO 2005/023282 | 3/2005 |
| WO | WO 2005/084678 | 9/2005 |
| WO | WO 2006/012692 | 2/2006 |
| WO | WO 2006/092024 | 9/2006 |
| WO | WO 2006/092025 | 9/2006 |
| WO | 2006/133506 | 12/2006 |
| WO | WO 2006133506 A1 * | 12/2006 |
| WO | WO 2007/070981 | 6/2007 |
| WO | 2007075883 | 7/2007 |
| WO | WO 2008/034178 | 3/2008 |
| WO | WO 2009/146443 | 12/2009 |

OTHER PUBLICATIONS

Phosphagenics Limited, Company Announcement, "First Subject Dosed in Phase 1B Clinical Trial of Phosphagenics' Patented Oxycodone Patch," Dec. 2, 2009 (2 pages).
Phosphagenics Limited, Company Announcement, "Insulin Patch on Track for Clinical Trials," Dec. 17, 2009 (2 pages).
Phosphagenics Limited, Company Announcement, "Phosphagenics Announces Completion of Transdermal Patch Prototypes," May 29, 2009 (2 pages).
Phosphagenics Limited, Company Announcement, "Phosphagenics Announces Successful Completion of its Transdermal Oxycodone Matrix Patch Phase 1 Trial," Sep. 15, 2009 (2 pages).
Phosphagenics Limited, Company Announcement, "Phosphagenics Announces the Successful completion of a Phase 1 Clinical Trial Using TPM/Oxycodone," Jun. 29, 2009 (2 pages).
Phosphagenics Limited, Company Announcement, "Phosphagenics to Present at ONEMEDFORUM 2010," Jan. 8, 2010 (28 pages).
Aberg, F. et al., "Distribution and redox state of ubiquinones in rat and human tissues," Arch. Biochem. Biophys. (1992) 295(2):230-234.
Almeida, M.E.M. et al., "Evaluation of soybean oil deodorization distillate for Vitamin E recovery," Arq. Biol. Tecnol. (1994) 37(4):1003-1011.
Anslyn, E.V. et al., Modern Physical Organic Chemistry. Chapter 3: Solutions and Non-Covalent Binding Forces. University Science Books. (2006) see p. 146.
Barrett, C.W. et al., "The effect of particle size and vehicle on the percutaneous absorption of fluocinolone acetonide," Brit. J. Dermatol. (1965) 77:576-578.
Bikerman, J.J., "Mechanical destruction of young and old foam films," J. Phys. Chem. (1952) 56:164-165.
Block, L.H., "Chapter 44: Medicated Topicals," in Remington: The Science and Practice of Pharmacy, 20th edition, Edited by Alfonso R. Gennaro, Baltimore, MD, Lippincott, Williams & Wilkins (2000) 836-857.
Blom, J.H. et al., "Reproductive success of female rainbow trout (Oncorhynchus mykiss) in response to graded dietary ascorbyl monophosphate levels," Biol. of Reproduction (1995) 52:1073-1080.
Blum, A. et al., "Clinical and inflammatory effects of dietary L-arginine in patients with intractable angina pectoris," Amer. J. Cardiol. (1999) 1488-1489.

(56) References Cited

OTHER PUBLICATIONS

Brandt, M., "Steroid hormone biosynthesis," (2002) printed from http://www.rose_hulman.edu/~brandt/Chem430/Steroids.pdf on Nov. 20, 2010 (7 pages).
Cevc, G. "Transdermal drug delivery of insulin with ultradeformable carriers," Clin. Pharmacokinet. (2003) 42(5):461-474.
Cevc, G. et al., "Ultraflexible vesicles, transfersomes, have an extremely low pore penetration resistance and transport therapeutic amounts of insulin across the intact mammalian skin," Biochim. Biophys. Acta (1998) 1368:201-215.
De Wolfe, F.A. et al., "Ligand-binding proteins: their potential for application in systems for controlled delivery and uptake of ligands," Pharmacol. Rev. (2000) 52(2):207-236.
Devaraj, S. et la., "Alpha tocopherol decreases CD36 expression in human monocyte-derived macrophages," J. Lipid Res. (2001) 42:521-527.
Devaraj, S. et al., "Modulation of monocyte-macrophage function with alpha-tocopherol: implications for atherosclerosis," Nat. Rev. (2002) 60(1):8-14.
Devaraj, S. et al., "Alpha tocopherol supplementation decreases serum C-reactive protein and monocyte interleukin-6 levels in normal volunteers and type 2 diabetic patients," Free Radic. Biol. Med. (2000) 29(8):790-792.
Ernster, L. et al., "Biochemical, physiological and medical aspects of ubiquinone function," Biochim. Biophys. Acta (1995) 1271:195-204.
Fracalossi, D.M. et al., "Oscars, Astronotus ocellatus, have a dietary requirement for vitamin C," J. Nutrition (1998) 128:1745-1751.
Frei, B. et al., "Ubiquinol-10 is an effective lipid-soluble antioxidant at physiological concentrations," Proc. Natl. Acad. Sci. (1990) 87:4879-4883.
Gann, P.H. et al., "Lower prostate cancer risk in men with elevated plasma lycopene levels: results of a prospective analysis," Cancer Res. (1999) 59(6):1225-1230.
Gianello, R. et al., "α-tocopheryl phosphate: a novel, natural form of vitamin E," Free Radical Biol. Med. (2005) 39:970-976.
Gianello, R. et al., "Subchronic oral toxicity study of mixed tocopheryl phosphates in rats," Int'l J. Toxicol. (2007) 26:475-490.
Godin, B. et al., "Ethosomes: new prospects in transdermal delivery," Crit. Rev. Thera. Drug Car. Syst. (2003) 20(1):63-102.
Goff et al., "Prevention of cardiovascular disease in persons with Type 2 diabetes mellitus: current knowledge and rationale for the action to control cardiovascular risk in diabetes (ACCORD) trial," Am. J. Cardiol. (2007) 99(suppl):4i-20i.
Griffin, E. et al., "A link between diabetes and atherosclerosis: glucose regulates expression of CD36 at the level of translation," Nature Med. (2001) 7(7):840-846.
Guo, J. et al., "Transdermal delivery of insulin in mice by using Lecithin vesicles as a carrier," Drug Del. (2000) 7:113-116.
Heron-Milhavet, L. et al., "Muscle-specific overexpression of CD36 reverses the insulin resistance and diabetes of MKR mice," Endocrinology (2004) 145:4667-4676.
Imada, I. et al., "Photochemical Reaction of Ubiquinone. IV. Coenzymatic activity of ubiquinone and related compounds," Chem. Pharm. Bull. (1965) 13:136-142.
Iimura, N. et al., "Complex formation between cationic surfactantsand insoluble drugs," Bull. Chem. Soc. Jpn. (1999) 72:2417-2422.
International Specialty Products,"A Product Guide. Performance enhancing Products for Pharmaceuticals," (2005) 20 pages [retrieved on Jul. 27, 2010 from http://web.archieve.org/web/20060623233652/http://abstracts.aapspharmaceutica.com/ExpoAAPS06/Data/EC/Event/Exhibitors/309/4ecb9a3a-65d0-4c69-a762-c60e099922ee.pdf, published on Jun. 23, 2006 as per Wayback Machine].
Isoda, K. et al., "Metformin inhibits proinflammatory responses and nuclear factor-κB in human vascular wall cells," Arterioscler. Thromb. Vasc. Biol. (2006) 26:611-617.
Jiang, Q. et al., "γ-tocopherol, the major form of vitamin E in the U.S. diet, deserves more attention," Am. J. Clin. Nutri. (2001) 74(6):714-722.
Kagan, V. et al., "Antioxidant effects of ubiquinones in microsomes and mitochondria are mediated by tocopherol recycling," Biochem. Biophys. Res. Commun. (1990) 169(3):851-857.
Karrer, V.P. et al., "d,l-alpha-tocopherol-phosphorsaure-ester," Zurich, Chemisches Institut der Universitat (1933) p. 1137-1138, in German.
King, M.J. et al., "Transdermal delivery of insulin from a novel biphasic lipid system in diabetic rats," Diab. Tech. Therap. (2002) 4(4):479-488.
Knowler, W.C. et al., "Preventing Non-insulin-dependent diabetes," Diabetes (1995) 44:483-488.
Langsjoen, P.H. et al., "Overview of the use of CoQ10 in cardiovascular diseases," Biofactors (1999) 9:273-284.
Lass, A. et al., "Electron transport-linked ubiquinone-dependent recycling of α-tocopherol inhibits autooxidation of mitochondrial membranes," Arch. Biochem. Biophys. (1998) 352(2):229-236.
Lee, C.-F. et al., "Attenuation of UV-induced apoptosis by coenzyme Q10 in human cells harboring large-scale deltion of mitochontrial DNA," Ann. N.Y. Acad. Sci. (2005) 1042:429-438.
Lei, B. et al.,. Progress in alpha-tocopherol preparation technology, Xiandai Huagong (1997) 17(7):13-15.
Libinaki, R. et al., "Evaluation of the safety of mixed tocopheryl phosphates (MTP)-a formulation of α-tocopheryl phosphate plus α-di-tocopheryl phosphate," Food Chem. Toxicol. (2006) 44(7):916-932.
Little, P.J. et al., "Phosphorylated troglitazone activates PPARγ and inhibits vascular smooth muscle cell proliferation and proteoglycan synthesis," J. Cardiovasc. Pharmacol. (2008) 51(3):274-279.
Maguire, J.J. et al., "Succinate-ubiquinone reductase linked recycling of alpha-tocopherol in reconstituted systems and mitochondria: requirement for reduced ubiquinone," Arch. Biochem. Biophys. (1992) 292(1):47-53.
Mellors, A. et al., "The inhibition of mitochondrial peroxidation by ubiquinone and ubiquinol," J. Biol. Chem. (1966) 241(19):4353-4356.
Merck Index, The, "α-estradiol" Thirteenth Edition, Whitehouse Station, NJ (2001) p. 660.
Merck Index, The, "Fludarabine to Fludeoxyglucose F18" pages, Thirteenth Edition, Whitehouse Station, NJ (2001) pp. 729-730.
Min, J. et al., "Effect of apoptosis induced by different vitamin E homologous analogues in human hepatoma cells (HepG2)," J. Hygiene Res. China (2003) 32(4):343-345.
Miyamoto, S. et al., "Synthesis of a novel phosphate ester of a vitamin E derivative and its antioxidative activity," Biosci. Biotech. Biochem. (1998) 62(12):2463-2466.
Morgan, T.M. et al., "Transdermal delivery of estradiol in postmenopausal women with a novel topical aerosol," J. Pharm. Sci. (1998) 87(10):1226-1228.
Morgan, T.M. et al., "Enhanced transdermal delivery of sex hormones in swine with a novel topical aerosol," J. Pharm. Sci. (1998) 87(10):1219-1225.
Mortensen, S.A., "Perspectives on therapy of cardiovascular diseases with coenzyme Q10 (ubiquinone)," Clin. Investig. (1993) 71(Suppl. 8): S116- S123.
Mottu, F. et al., "Organic solvents for pharmaceutical parenterals and embolic liquids: a review of toxicity data," PDA Journal of Pharm. Sci. Tech. (2000) 54(6):456-469.
Mukherjee, S. et al., "Cardioprotection with α-tocopheryl phosphate: amelioration of myocardial ischemia reperfusion injury is linked with its ability to generate a survival signal through Akt activation," Biochim. Biophys. Acta (2008) 1782:498-503.
Munteanu, A. et al., "Modulation of cell proliferation and gene expression by alpha-tocopheryl phosphates: relevance to atherosclerosis and inflammation," Biochem. Biophys. Res. Comm. (2004) 318(1):311-316.
Nakayama, S. et al., "Protective effects of a stable, water-soluble vitamin E on photodamage induced by UVB irradiation in cultured mouse skin," Photomedicine and Photobiology (1998) 20:99-100.
Negis, Y. et al., "On the existence of cellular tocopheryl phosphate, its synthesis, degradation and cellular roles: a hypothesis," IUBMB Life (2005) 57(1):23-25.

(56) References Cited

OTHER PUBLICATIONS

Negis, Y. et al., "Molecular mechanism of alpha-tocopheryl-phospate transport across the cell membrane," Biochem. Biophys. Res. Comm. (2007) 359:348-353.

Negis, Y. et al., "The effect of tocopheryl phosphates on atherosclerosis progression in rabbits fed with a high cholesterol diet," Arch. Biochem. Biophys. (2006) 450:63-66.

Octoplus, "Formulation Development of Poorly Soluble Drugs" (www.octoplus.nl) (1999) 2 pages. (downloaded Nov. 2008).

Ogru, E. et al., "Vitamin E phosphate: an endogenous form of vitamin E," Medimond S.r.l. (2003) 127-132.

Ostrenga, J. et al., "Significance of vehicle composition I: Relationship between topical vehicle composition, skin penetrability, and clinical efficacy," J. Pharm. Sci. (1971) 60(8):1175-1179.

Owens, D.R. et al., "Alternative routes of insulin delivery," Diabet. Med. (2003) 20:886-898.

Parker et al., "Neonatal vitamin K administration and childhood cancer in the North of England: retrospective case-control study," BMJ (1998) 316:189-193.

Potts, R.O. et al., "Predicting skin permeability," Pharm. Res. (1992) 9(5):663-669.

Puratchikody, A. et al., "Reverse phase—high performance liquid chromatographic determination of atorvastatin calcium in solid dosage forms," Pharma. Review (2003) 1(2):79-80, 83—STN File CA, Abstract 139:399976 only.

Rerek, M.E. et al., "Disodium lauriminodipropionate tocopheryl phosphates: a potent new anti-inflammatory," Cosmetics & Toiletries magazine (2003) 118(7):63-67.

Rezk, B.M. et al., "The extraordinary antioxidant activity of vitamin E phosphate," Biochim. Biophys. Acta (2004) 1683:16-21.

Ricciarelli, R. et al., "Vitamin E reduces the uptake of oxidized LDL by inhibiting CD36 scavenger receptor expression in cultured aortic smooth muscle cells," Circulation (2000) 102:82-87.

Schwenke, D.C. et al., "α-tocopherol protects against diet induced atherosclerosis in New Zealand white rabbits," J. Lipid Res. (2002) 43:1927-1938.

Sevast'Ianov, V.I. et al., "Transdermal delivery of insulin," Meditsinskaia Tekhnika (2003) 2:21-24.

Seyama, Y. et al., "Comparative effects of Vitamin K2 and estradiol on experiemental arteriosclerosis with diabetes mellitus," Int. J. Vitam. Nutr. Res. (2000) 70(6):301-304, Abstract only.

Singh, R.B. et al., "Randomized double-blind placebo-controlled trial of coenzyme Q10 in patients with acute myocardial infarction," Cardiov. Drugs Ther. (1998) 12:347-353.

Stedman's Medical Dictionary, "Tocopherol," "Tocotrienol," and "Vitamin K1", 22nd Edition, Williams & Wilkins Co. (1972) p. 1303 and 1400.

Suzuki, T. et al., "The solution behavior and the association structure of long-chain monoalkyl phosphates," Chem. Soc. Japan (1986) 633-640, with English abstract.

Teupser, D. et al., "Alpha-tocopherol down-regulates scavenger receptor activity in macrophages," Atherosclerosis (1999) 144:109-115.

Traber, M.G. et al., "Human plasma vitamin E kinetics demonstrates rapid recycling of plasma RRR-alpha-tocophero," Proc. Natl. Acad. Sci. USA (1994) 91:10005-10008.

Visarius, T. et al., "Inhibition of human prostate cancer cell proliferation: vitamin E and lycopene targeted pathways regulating cell cycle progression," FASEB J. (2004) 18(8):C103.

Walters et al., "The effects of surfactants on penetration across the skin," Inter. J. Cosmetic Sci. (1993) 15:260-270.

Williams, A.C. et al., "Penetration enhancers," Advanced Drug Delivery Reviews (2004) 56(5):603-618.

Younis et al., "The prevention of type 2 diabetes mellitus: recent advances," Q.J. Med. (2004) 97:451-455.

United States Office Action for U.S. Appl. No. 09/979,436 dated Apr. 4, 2002 (6 pages).

United States Office Action for U.S. Appl. No. 09/979,436 dated Sep. 23, 2002 (6 pages).

United States Office Action for U.S. Appl. No. 10/416,775 dated Nov. 2, 2005 (10 pages).

United States Office Action for U.S. Appl. No. 10/416,775 dated Jun. 12, 2006 (10 pages).

United States Office Action for U.S. Appl. No. 10/416,775 dated Jul. 12, 2007 (11 pages).

United States Office Action for U.S. Appl. No. 10/416,775 dated Dec. 17, 2008 (6 pages).

United States Patent Office Action for U.S. Appl. No. 12/628,443 dated Feb. 18, 2011 (15 pages).

United States Patent Office Action for U.S. Appl. No. 12/628,443 dated Aug. 5, 2011 (8 pages).

United States Patent Office Notice of Allowance for U.S. Appl. No. 12/628,443 dated Jan. 12, 2012 (7 pages).

United States Office Action for U.S. Appl. No. 10/416,774 dated Sep. 6, 2007 (9 pages).

United States Office Action for U.S. Appl. No. 10/416,774 dated Jun. 11, 2008 (15 pages).

United States Office Action for U.S. Appl. No. 10/416,774 dated Feb. 17, 2009 (15 pages).

United States Office Action for U.S. Appl. No. 10/416,774 dated Apr. 15, 2009 (14 pages).

United States Patent Office Action for U.S. Appl. No. 10/416,774 dated Dec. 18, 2009 (11 pages).

United States Office Action for U.S. Appl. No. 10/462,480 dated Dec. 1, 2006 (10 pages).

United States Office Action for U.S. Appl. No. 10/462,480 dated Nov. 1, 2007 (10 pages).

United States Office Action for U.S. Appl. No. 10/462,480 dated Feb. 20, 2009 (17 pages).

United States Patent Office Action for U.S. Appl. No. 10/462,480 dated Nov. 27, 2009 (9 pages).

United States Patent Office Action for U.S. Appl. No. 12/768,307 dated Oct. 6, 2011 (13 pages).

United States Office Action for U.S. Appl. No. 10/485,196 dated May 29, 2008 (23 pages).

United States Office Action for U.S. Appl. No. 10/485,196 dated Jul. 23, 2009 (9 pages).

United States Patent Office Action for U.S. Appl. No. 10/485,196 dated Jan. 25, 2010 (8 pages).

United States Patent Office Action for U.S. Appl. No. 10/485,196 dated Oct. 29, 2010 (13 pages).

United States Patent Office Notice of Allowance for U.S. Appl. No. 10/485,196 dated Apr. 14, 2011 (7 pages).

United States Office Action for U.S. Appl. No. 10/486,142 dated Mar. 18, 2008 (12 pages).

United States Patent Office Action for U.S. Appl. No. 12/212,803 dated Mar. 12, 2010 (13 pages).

United States Office Action for U.S. Appl. No. 10/487,743 dated Dec. 2, 2005 (22 pages).

United States Office Action for U.S. Appl. No. 10/487,743 dated Jul. 27, 2006 (23 pages).

United States Office Action for U.S. Appl. No. 10/498,684 dated Oct. 2, 2008 (21 pages).

United States Office Action for U.S. Appl. No. 10/498,684 dated Jun. 23, 2009 (19 pages).

United States Patent Office Action for U.S. Appl. No. 10/498,684 dated Jul. 7, 2010 (21 pages).

United States Office Action for U.S. Appl. No. 10/524,090 dated Mar. 12, 2008 (12 pages).

United States Patent Office Action for U.S. Appl. No. 10/524,090 dated Mar. 3, 2010 (18 pages).

United States Patent Office Action for U.S. Appl. No. 10/524,090 dated Nov. 23, 2010 (19 pages).

United States Office Action for U.S. Appl. No. 10/542,511 dated Aug. 8, 2007 (19 pages).

United States Office Action for U.S. Appl. No. 10/542,511 dated Mar. 31, 2008 (20 pages).

United States Office Action for U.S. Appl. No. 10/542,511 dated Feb. 5, 2009 (23 pages).

United States Patent Office Action for U.S. Appl. No. 10/542,511 dated Jan. 12, 2010 (13 pages).

(56) References Cited

OTHER PUBLICATIONS

United States Patent Office Advisory Action for U.S. Appl. No. 10/542,511 dated May 25, 2010 (3 pages).
United States Patent Office Action for U.S. Appl. No. 12/834,553 dated Apr. 14, 2011 (13 pages).
United States Patent Office Action for U.S. Appl. No. 12/834,553 dated Oct. 7, 2011 (11 pages).
United States Office Action for U.S. Appl. No. 10/551,200 dated Jan. 28, 2009 (11 pages).
United States Office Action for U.S. Appl. No. 10/551,201 dated Jan. 24, 2008 (6 pages).
United States Office Action for U.S. Appl. No. 10/551,203 dated Dec. 6, 2006 (13 pages).
United States Office Action for U.S. Appl. No. 10/551,203 dated Sep. 7, 2007 (13 pages).
United States Office Action for U.S. Appl. No. 10/551,203 dated Apr. 11, 2008 (11 pages).
United States Office Action for U.S. Appl. No. 10/551,203 dated Dec. 19, 2008 (13 pages).
United States Office Action for U.S. Appl. No. 10/551,203 dated Jul. 21, 2009 (21 pages).
United States Patent Office Action for U.S. Appl. No. 12/690,735 dated Sep. 27, 2011 (15 pages).
United States Patent Office Action for U.S. Appl. No. 11/572,864 dated Mar. 15, 2012 (15 pages).
United States Patent Office Action for U.S. Appl. No. 11/817,439 dated Nov. 24, 2010 (15 pages).
United States Patent Office Action for U.S. Appl. No. 11/817,439 dated May 11, 2011 (11 pages).
United States Patent Office Action for U.S. Appl. No. 11/817,439 dated Jul. 29, 2011 (2 pages).
United States Patent Office Action for U.S. Appl. No. 11/817,453 dated Oct. 9, 2009 (11 pages).
United States Patent Office Action for U.S. Appl. No. 11/817,453 dated Aug. 2, 2010 (10 pages).
United States Patent Office Action for U.S. Appl. No. 11/817,453 dated Mar. 9, 2011 (12 pages).
United States Patent Office Action for U.S. Appl. No. 11/817,453 dated Oct. 13, 2011 (14 pages).
United States Patent Office Action for U.S. Appl. No. 11/917,831 dated Jan. 19, 2011 (10 pages).
United States Patent Office Action for U.S. Appl. No. 11/917,831 dated Oct. 24, 2011 (11 pages).
United States Patent Office Action for U.S. Appl. No. 12/158,932 dated Aug. 19, 2010 (15 pages).
United States Patent Office Action for U.S. Appl. No. 12/782,560 dated Sep. 1, 2011 (18 pages).
United States Patent Office Action for U.S. Appl. No. 12/782,564 dated Sep. 1, 2011 (20 pages).
Guthrie et al., VIIth Asian Conference of Nutrition: Lipid Symposium Proceedings, Journal of Nutrition, 1997, vol. 127, pp. 544s-548s.
Jiang, Q. et al., "γ-tocopherol induces apoptosis in androgen-responsive LNCaP prostate cancer cells via caspase-dependent and independent mechanisms," Annals of the New York Academy of Sciences, 2004, vol. 103, pp. 399-400.
Koh, "Antioxidants in a carotenoid-rich edible oil," Journal of Japan Mibyou System Association, 2003, vol. 9, No. 1, pp. 12-13.
Pastori et al., "Lycopene in association with α-tocopherol inhibits at physiological concentrations proliferation of prostate carcinoma cells," Biochemical and Biophysical Research Communications, 1998, vol. 250, pp. 582-585.
International Preliminary Report on Patentability from PCT/AU2011/000358, dated May 22, 2012—47 pgs.
United States Patent Office Action for U.S. Appl. No. 12/782,560 dated May 24, 2012 (22 pages).
United States Patent Office Action for U.S. Appl. No. 12/782,564 dated May 24, 2012 (25 pages).
United States Patent Office Action for U.S. Appl. No. 12/690,735 dated Aug. 2, 2012 (9 pages).
United States Patent Office Action for U.S. Appl. No. 12/782,438 dated Aug. 30, 2012 (14 pages).
United States Patent Office Action for U.S. Appl. No. 11/572,864 dated Nov. 8, 2012 (16 pages).
Sinha, V.R. et al., "Coating polymers for colon specific drug delivery: A comparative in vitro evaluation," Acta. Pharm., 2003, vol. 53, pp. 41-47.
United States Patent Office Action for U.S. Appl. No. 11/817,439 dated Nov. 7, 2012 (10 pages).
United States Patent Office Action for U.S. Appl. No. 13/501,494 dated Dec. 18, 2012 (13 pages).
Sharma H. et al., "An excerpt from the medical textbook Contemporary Ayurverda," Edinburgh: Churchill Livingston, 1998, 6 pages, Retrieved from Internet on Nov. 1, 2012 <URL: http://www.bsherman.net/freeradicals.htm>.
International Search Report and Written Opinion for Application No. PCT/AU2011/000358 dated May 31, 2011 (10 pages).
Written Opinion for Application No. PCT/AU2011/000358 dated Feb. 21, 2012 (7 pages).
United States Patent Office Action for U.S. Appl. No. 13/577,124 dated Feb. 14, 2013 (15 pages).
United States Patent Office Action for U.S. Appl. No. 13/501,498 dated Feb. 21, 2013 (12 pages).
Maugard et al., "Synthesis of Water-Soluble Retinol Derivatives by Enzymatic Method," Biotechnol. Prog., 2002, vol. 18, pp. 424-428.
United States Patent Office Action for U.S. Appl. No. 13/683,698 dated Apr. 24, 2013 (18 pages).
United States Patent Office Action for U.S. Appl. No. 11/572,864 dated Sep. 16, 2013 (10 pages).
United States Patent Office Final Rejection for U.S. Appl. No. 13/501,494 dated Aug. 22, 2013 (13 pages).
United States Patent Office Action for U.S. Appl. No. 13/501,499 dated Sep. 25, 2013 (12 pages).
United States Patent Office Final Rejection for U.S. Appl. No. 13/577,124 dated Aug. 2, 2013 (14 pages).
Li et al ("Effect of HPMC and Carbopol on the release and floating properties of gastric floating drug delivery system using factorial design." International Journal of Pharmaceutics, 2003; 253:13-22.).
Barry ("Novel mechanisms and devices to enable successful transdermal drug delivery." Sciences, 2001; 14:101-114).
United States Patent Office Final Rejection for U.S. Appl. No. 13/683,698 dated Nov. 14, 2013 (15 pages).
United States Patent Office Final Rejection for U.S. Appl. No. 13/501,498 dated Nov. 14, 2013 (10 pages).
Squillante et al, European Journal of Pharmaceutics and Biopharmaceutics 46 (1998) 265-271.

\* cited by examiner

Backing material
Matrix film
Packaging liner

TRANSDERMAL DELIVERY PATCH

CROSS-REFERENCE TO RELATED APPLICATIONS

This is a national stage filing under 35 U.S.C. §371 of International Application No. PCT/AU2011/000358, filed on Mar. 30, 2011, which claims the benefit of priority to U.S. Provisional Application No. 61/319,002, filed on Mar. 30, 2010, and U.S. Provisional Application No. 61/319,007, filed on Mar. 30, 2010.

TECHNICAL FIELD

The present invention relates to a composition suitable for use in a transdermal delivery patch for administration of a biologically active compound, and a transdermal delivery patch comprising the composition, or matrix layer.

BACKGROUND

In this specification where a document, act or item of knowledge is referred to or discussed, this reference or discussion is not an admission that the document, act or item of knowledge or any combination thereof was at the priority date, publicly available, known to the public, part of common general knowledge; or known to be relevant to an attempt to solve any problem with which this specification is concerned.

Drug delivery is the method or process of administering a pharmaceutical compound to achieve a therapeutic effect in humans and animals.

Drug delivery technologies have been developed to improve bioavailability, safety, duration, onset or release, of the pharmaceutical compound.

When developing drug delivery technologies, problems likely to be encountered include compatibility of the drug delivery system and the pharmaceutical compound, maintaining an adequate and effective duration, potential for side effects, and meeting patient convenience and compliance. As a consequence, many drug delivery technologies fall short of desired improvements and requirements.

Accordingly, there is still a need for alternate delivery systems that effectively deliver drugs and other biologically active compounds.

SUMMARY

The present invention relates to a composition suitable for use in a transdermal delivery patch for administration of a biologically active compound, and a transdermal delivery patch comprising the composition, or matrix layer.

Accordingly, a first aspect of the present invention provides a matrix layer for use in a transdermal delivery patch for administration of a biologically active compound, the matrix layer comprising a mixture of a mono-tocopheryl phosphate compound and a di-tocopheryl phosphate compound and a polymer carrier wherein the polymer carrier is present in an amount within the range of about 30% w/w to about 95% w/w.

The present invention also provides use of the composition, or matrix layer, in a transdermal delivery patch for administration of a biologically active compound.

It has surprisingly been found that biologically active compounds can be effectively administered using a transdermal delivery patch.

A second aspect of the present invention provides a transdermal delivery patch for administration of a biologically active compound comprising the composition, or matrix layer. The composition, or matrix layer, may be a solid or semi-solid layer. The transdermal delivery patch may comprise further layers.

A third aspect of the present invention provides a method for preparing a transdermal delivery patch for administration of a biologically active compound comprising the steps of:
  (i) combining a polymer carrier and optional inert carrier components with a suitable solvent;
  (ii) combining (i) with a dispersion comprising a biologically active compound and a mixture of a mono-tocopheryl phosphate compound and a di-tocopheryl phosphate compound;
  (iii) stirring (ii) until complete homogenisation is achieved;
  (iv) placing the composition of (iii) in a suitable mould or casting the composition of (iii) on a surface;
  (v) drying the composition under heat.

DETAILED DESCRIPTION

The present invention relates to a composition suitable for use in a transdermal delivery patch for administration of a biologically active compound, the composition comprising a phosphate compound of tocopherol and a polymer carrier. The composition, or matrix layer, may form part of a transdermal delivery matrix patch. It has been surprisingly found that a transdermal delivery patch comprising this composition, or matrix layer, can effectively administer biologically active compounds.

Tocopheryl Phosphate Compound

The composition, or matrix layer, comprises a mixture of a mono-tocopheryl phosphate compound and a di-tocopheryl phosphate compound.

Vitamin E exists in eight different forms, namely four tocopherols and four tocotrienols. All feature a chroman ring, with a hydroxyl group that can donate a hydrogen atom to reduce free radicals and a hydrophobic side chain which allows for penetration into biological membranes. Such derivatives of vitamin E may be classified as "hydroxy chromans". Both tocopherols and tocotrienols occur in alpha, beta, gamma and delta forms, determined by the number and location of methyl groups on the chroman ring. The tocotrienols differ from the analogous tocopherols by the presence of three double bonds in the hydrophobic side chain. The various forms of vitamin E are shown by Formula (I):

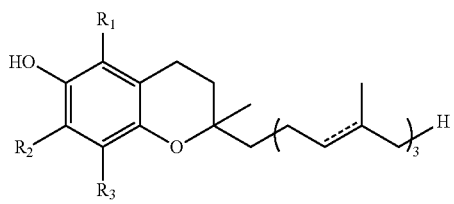

|  | $R_1$ | $R_2$ | $R_3$ |
|---|---|---|---|
| α-tocopherol<br>α-tocotrienol | $CH_3$ | $CH_3$ | $CH_3$ |
| β-tocopherol<br>β-tocotrienol | $CH_3$ | H | $CH_3$ |
| γ-tocopherol<br>γ-tocotrienol | H | $CH_3$ | $CH_3$ |
| δ-tocopherol<br>δ-tocotrienol | H | H | $CH_3$ |

In the present invention, tocopherol in any of the four forms may be used. The alpha form of tocopherol is preferred.

The term "phosphate compound" refers to phosphorylated tocopherol, where a covalent bond is formed between an oxygen atom (typically originating from a hydroxyl group) of the tocopherol compound and the phosphorous atom of a phosphate group ($PO_4$).

The phosphate compound may be a phosphate mono-ester, phosphate di-ester, phosphate tri-ester, pyrophosphate mono-ester, pyrophosphate di-ester, or a salt or derivative thereof, or a combination thereof. The di- and tri-esters may comprise the same tocopherol form or different tocopherol forms.

The "salts" include metal salts such as alkali or alkaline earth metal salts, for example sodium, magnesium, potassium and calcium salts. Sodium and potassium salts are preferred.

The "derivatives" include phosphate compounds where one or more phosphate protons are replaced by a substituent. Some non-limiting examples of derivatives include phosphatidyl derivatives where a phosphate proton is substituted with an amino-alkyl group, sugar derivatives where a phosphate proton is substituted with a sugar such as glucose.

The term "amino-alkyl group" refers to a group comprising an amino ($-NH_2$) group and an alkyl group. The term "alkyl" refers to straight chain, branched chain or cyclic hydrocarbon groups having from 1 to 8 carbon atoms. Examples include methyl, ethyl, propyl, isopropyl, butyl, isobutyl, sec-butyl, tert-butyl, pentyl, hexyl, cyclohexyl, heptyl, and octyl. Phosphatidyl choline derivatives are most preferred.

The mono-tocopheryl phosphate compound may be selected from the group consisting of mono-(tocopheryl) phosphate, mono-(tocopheryl)phosphate monosodium salt, mono-(tocopheryl)phosphate disodium salt, mono-(tocopheryl)phosphate monopotassium salt and mono-(tocopheryl)phosphate dipotassium salt, and the di-tocopheryl phosphate compound may be selected from the group consisting of di-(tocopheryl)phosphate, di-(tocopheryl)phosphate monosodium salt and di-(tocopheryl)phosphate monopotassium salt. These phosphate compounds may be derived from the alpha, beta, gamma or delta form of tocopherol, or a combination thereof.

When a combination of a mono-phosphate ester and a di-phosphate ester, that is a mono-(tocopheryl)phosphate and di-(tocopheryl)phosphate (which may in some instances herein be referred to as tocopheryl phosphate mixture or simply "TPM"), the ratio (% w/w) is at least 2:1, within a range of about 4:1 to about 1:4, within a range of about 6:4 to about 8:2. The ratio may be about 2:1, about 6:4, or about 8:2.

The mixture of the mono-tocopheryl phosphate compound and the di-tocopheryl phosphate compound may be present in an amount within a range of about 0.01% w/w to about 10% w/w, within the range of about 0.1% w/w to about 5% w/w, within the range of about 0.1% w/w to about 3% w/w, within the range of about 0.1% w/w to about 2% w/w, within the range of about 0.1% w/w to about 1% w/w or within the range of about 0.1% w/w to about 0.5% w/w, of the total concentration of the composition, or matrix layer. In some embodiments, the mixture of the mono-tocopheryl phosphate compound and the di-tocopheryl phosphate compound may be present in an amount within a range of about 0.5% w/w to about 1.5% w/w, or in an amount of about 0.1% w/w, of the total concentration of the composition, or matrix layer.

Polymer Carrier

The composition, or matrix layer, also comprises a polymer carrier.

The polymer carrier may comprise natural and synthetic polymers, co-polymers, or terpolymers.

Natural polymers include rubbers, elastomers, polysaccharides such as cellulose, natural resins such as shellac and amber.

Synthetic polymers include, for example, acrylates, polyacrylates, polyalkyl acrylates, polyamides, polyesters, polycarbonates, polyimides, polystyrenes, acrylonitrile butadiene styrene, polyacrylonitrile, polybutadiene, poly(butylene terephthalate), poly(ether sulphone), poly(ether)ketones, polyethylene, poly(ethylene glycol), poly(ethylene teraphthalate), polypropylene, polytetratfluoroethylene, styrene-acrylonitrile resin, poly(trimethylene terephthalate), polyurethanes, polyvinyl butyral, polyvinylchlorides, polyvinylidenedifluoride, povidones, poly(vinyl pyrrolidone), polychloroprene, fluoroelastomers, chloro-sulphonated rubbers, hypromellose, polyolefine elastomer, polyacrylamide, chlorinated polyethylene, polyethersulphone, nylon, liquid crystal polymers, polyethylene terephthalate (PET), polyphenylsulphone, polypthalaminepolyvinyl alcohol derivatives, poly ethylene glycols, ethylene vinyl acetate, polymethyl methacrylate, cellulose derivatives such as ethyl cellulose, hydroxylpropyl methyl cellulose, sugar derivatives (gums) including derivatives of sorbitol and mannitol, silicone oil and silicone oil derivatives, polysiloxanes including amine-resistant polysiloxanes, and siloxanes.

Preferred polymer carriers suitable for use in the composition, or matrix layer, of the present invention include acrylates, povidones and siloxanes. Particularly preferred polymer carriers include polyvinyl pyrrolidone (e.g. PVP K90, MW 360,000 Da), polysiloxanes, polyalkyl acrylates (e.g. DuroTak) and polymethyl methacrylate (e.g. Eudragit E100). In one embodiment, the polymer carrier is polyvinyl pyrrolidone. In an alternate embodiment, the polymer carrier is polymethyl methacrylate.

The polymer carrier used in the composition, or matrix layer, may have sufficient tackiness to enable the transdermal delivery patch to adhere to skin. For instance, amine-resistant polysiloxanes and combinations thereof can be used in the composition, or matrix layer. A combination of a polysiloxane of medium tack and a polysiloxane of high tack is used would be most suitable. The polysiloxanes may be synthesized from linear bifunctional and branched polyfunctional oligomers. It has been found that the ratio of both types of oligomers determines the physical properties of the polymers. More polyfunctional oligomers result in a more crosslinked polymer with a higher cohesion and a reduced tack, less polyfunctional oligomers result in a higher tack and a reduced cohesion. A high tack version should be tacky enough for the transdermal delivery patch to adhere to the surface of skin. A medium tack version, on the other hand, may not be tacky at all but could be useful by providing a softening effect to other components included in the composition, or matrix layer. To increase the adhesive power of the composition, or matrix layer, a silicone oil (e.g. dimethicone) could be added.

The polymer carrier may be present in an amount within the range of about 30% w/w to about 95% w/w, within the range of about 30% w/w to about 80% w/w, or within the range of about 55% w/w to about 65% w/w, of the total weight of the composition, or matrix layer.

The polymer carrier may also comprise inert carrier components, such as for example, anti-tacking agents, tackifiers, and plasticizers to achieve appropriate softness, flexibility and "tackiness" for the polymer carrier to enable the composition, or matrix layer, to adhere to the surface of skin, and thus provide consistent delivery.

For polymers which are naturally "tacky" and may need anti-tackiness to have an appropriate consistency, anti-tacking agents that are solid with no stickiness property (i.e. low ability to retain solvents upon drying) and that can be mixed well (i.e. do not crystallise upon drying) with the polymer carrier may be suitable. The selection would be based on the polymer-type. Many surfactants are suitable for use as an anti-tacking agent with a polymer carrier. A more specific example of an anti-tacking agent is succinic acid. In specific embodiments, the anti-tacking agent may be present in an amount or less than 1% w/w, up to about 1% w/w, or up to about 5% w/w, of the total weight of the composition, or matrix layer.

In order to enhance the ability of the composition, or matrix layer, to adhere to the surface of skin, it may optionally contain a tackifier (or tacking agent). Tack can be controlled by combining adhesives of varying hardnesses (glass temperature or $T_g$). Typically, a tackifier is a polymer which is insoluble in water and composed of a monomer which contains partly or wholly a (meth)acrylic alkyl ester. Such types of polymers include, but are not limited to, acrylic, N-butyl-methacrylic copolymer (Primal N580NF, sold by Japan Acrylic Chemical Company, Ltd.), acrylic methyl, acrylic 2-ethylhexyl copolymer (Nikasol TS-6520, sold by Nippon Carbide Industries Company, Ltd), polyacrylic acid (Jurymer AC-IOLPH, sold by Nihon Junyaku Company, Ltd), methacrylic copolymer L (Plastoid L50, sold by Rohm Pharma GmbH), and aminoalkylmethacrylate copolymer E (Plastoid E35L, Plastoid E35M, Plastoid E35H, all sold by Rohm Pharma GmbH). Other non-limiting examples include rosin esters, hydrogenated rosins, dipropylene glycol dibenzoate, and/or mixed hydrocarbons, and acrylic copolymers (e.g. Flexbond 150 adhesive by Air Products).

Plasticizers are additives that increase the plasticity or fluidity of the material to which they are added. Plasticizers may be used in the present invention to soften the final product increasing its flexibility and making it less brittle. Suitable plasticizers include phthalates, esters of polycarboxylic acids with linear or branched aliphatic alcohols of moderate chain length, acetylated monoglycerides, alkyl citrates, triethyl citrate (TEC), acetyl triethyl citrate (ATEC), tributyl citrate (TBC), acetyl tributyl citrate (ATBC), trioctyl citrate (TOC), acetyl trioctyl citrate (ATOC), trihexyl citrate (THC), acetyl trihexyl citrate (ATHC), butyryl trihexyl citrate (BTHC, trihexyl o-butyryl citrate), trimethyl citrate (TMC), methyl laurate, lauric acid, lauryl lactate, lauryl alcohol, alkyl sulphonic acid phenyl ester, diethylene glycol monoethyl ether, bis(2-ethylhexyl)phthalate (DEHP), diisooctyl phthalate (DIOP), bis(n-butyl)phthalate (DnBP, DBP), diisobutyl phthalate (DIBP), bis(2-ethylhexyl)adipate (DEHA), dimethyl adipate (DMAD), monomethyl adipate (MMAD), dioctyl adipate (DOA), ethyl oleate, sorbitan monooleate, glycerol monooleate, dibutyl sebacate (DBS), dibutyl maleate (DBM), diisobutyl maleate (DIBM), benzoates, epoxidized vegetable oils, tris(tromethamine), N-ethyl toluene sulfonamide (o/p ETSA), N-(2-hydroxypropyl)benzene sulfonamide (HP BSA), N-(n-butyl)benzene sulfonamide (BBSA-NBBS), tricresyl phosphate (TCP), tributyl phosphate (TBP), triethylene glycol dihexanoate (3G6, 3GH), tetraethylene glycol diheptanoate (4G7), 1,3-butyleneglycol, dipropylene glycol, PEG400, Span 80, and polyvinylpyrrolidone. Dibutyl sebacate (DBS), sorbitan monooleate, methyl laurate and lauric acid are preferred plasticizers.

Inert carrier components may be present in an amount within the range of about 0.001% w/w to about 50% w/w, within the range of about 0.001% w/w to about 40% w/w, within the range of about 0.001% w/w to about 30% w/w, of the total weight of the composition, or matrix layer. In one embodiment, the composition, or matrix layer comprises an anti-tacking agent (such as succinic acid) and a plasticizer (such as dibutyl sebacate) in a total amount of about 35% w/w of the total weight of the composition, or matrix layer.

The amount of polymer carrier and optional inert carrier components present in the composition, or matrix layer will depend on the specific biologically active compound to be administered. Generally, however, these components may be present in an amount within the range of about 50% w/w to about 99% w/w, within the range of about 80% w/w to about 98% w/w, within the range of about 90% w/w to about 98% w/w, of the total weight of the composition, or matrix layer. In one embodiment, the composition, or matrix layer, comprises these components in the amount of about 95% w/w of the total weight of the composition, or matrix layer.

It should be noted that, in some instances herein, the term "polymer carrier" could be used collectively to refer to the polymer carrier and the inert carrier components.

The composition, or matrix layer, may also optionally further comprise one or more excipients (in addition to the inert carrier components discussed above).

A person skilled in the art of the invention would appreciate what are suitable excipients for inclusion in the composition, or matrix layer, of the invention. Some examples include, but are not limited to, solvents, thickeners or gelling agents, preservatives, surfactants, stabilizers, buffers, emollients, colours, fragrances, and appearance modifiers. It will be appreciated that any excipients which have been approved for use in pharmaceutical products by the regulatory bodies may be employed in the composition, or matrix layer, of the present invention. The amount of a particular excipient or excipients to be used in a composition, or matrix layer, of the present invention would also be appreciated by a person skilled in the art.

Biologically Active Compounds

The composition, or matrix layer, may form part of a transdermal delivery matrix patch. It has been surprisingly found that a transdermal delivery patch comprising this composition, or matrix layer, can effectively administer biologically active compounds.

The term "biologically active compound" refers to any chemical substance that has a biological effect in humans or animals for medical, therapeutic, cosmetic and veterinary purposes, and encompasses pharmaceuticals including drugs, cosmeceuticals, nutraceuticals, and nutritional agents. It will be appreciated that some of biologically active compounds can be classified in more than one of these classes.

A wide range of biologically active compounds may be delivered with the transdermal delivery patch of the present invention. Examples include, but are not limited to, cardiovascular drugs, in particular antihypertensive agents (e.g. calcium channel blockers or calcium antagonists) and antiarrhythmic agents; congestive heart-failure pharmaceuticals; inotropic agents; vasodilators; ACE inhibitors; diuretics; carbonic anhydrase inhibitors; cardiac glycosides; phosphodiesterase inhibitors; a blockers; β-blockers; sodium channel blockers; potassium channel blockers; β-adrenergic agonists; platelet inhibitors; angiotensin II antagonists; anticoagulants; thrombolytic agents; treatments for bleeding; treatments for anaemia; thrombin inhibitors; antiparasitic agents; antibacterial agents; insulin; human growth hormone and peptides; vaccines; antiinflammatory agents, in particular non-steroidal antiinflammatory agents (NSAIDs), more particularly COX-2 inhibitors; steroidal antiinflammatory agents; prophylactic antiinflammatory agents; antiglaucoma agents; mast cell stabilisers; mydriatics; agents affecting the respiratory system; allergic rhinitis pharmaceuticals; alpha-adrenergic agonists; corticosteroids; chronic obstructive pulmonary disease pharmaceuticals; xanthine-oxidase inhibitors; antiarthritis agents; gout treatments; autacoids and autacoid antagonists; antimycobacterial agents; antifungal agents; antiprotozoal agents; anthelmintic agents; antiviral agents especially for respiratory, herpes, cyto-megalovirus, human immunodeficiency virus and hepatitis infections; treatments for leukemia and kaposi's sarcoma; pain management agents in particular opioids, anaesthetics and analgesics; neuroleptics; sympathomimetic pharmaceuticals; adrenergic agonists; drugs affecting neurotransmitter uptake or release; anticholinergic pharmaceuticals; antihaemorrhoid treatments; agents to prevent or treat radiation or chemotherapeutic effects; liopgenisis drugs; fat reducing treatments; anti-obesity peptides; antiobesity agents such as lipase inhibitors; sympathomimetic agents; treatments for gastric ulcers and inflammation such as proton pump inhibitors; prostaglandins; VEGF inhibitors; antihyperlipidemic agents, in particular statins; drugs that affect the central nervous system (CNS) such as antipsychotic, antiepileptic and antiseizure drugs (anticonvulsants), psychoactive drugs, stimulants, antianxiety and hypnotic drugs, antidepressant drugs; antiparkinson's pharmaceuticals; hormones and fragments thereof such as sex hormones; growth hormone antagonists; gonadotropin releasing hormones and analogues thereof; steroid hormones and their antagonists; selective estrogen modulators; growth factors; antidiabetic pharmaceuticals such as insulin, insulin fragments, insulin analogues, glucagon-like peptides and hypoglycaemic agents; H1, H2, H3 and H4 antihistamines; peptide, protein, polypeptide, nucleic acids and oligonucleotide pharmaceuticals; analogues, fragments and varients of natural proteins, polypeptides, oligonucleotides and nucleic acids and such like compounds; agents used to treat migraine headaches; asthma pharmaceuticals; cholinergic antagonists; glucocorticoids; androgens; antiandrogens; inhibitors of adrenocorticoid biosynthesis; osteoporosis treatments such as biphosphonates; antithyroid pharmaceuticals; suncreens, sun protectants and filters; cytokine agonists; cytokine antagonists; anticancer drugs; antialzheimer drugs; HMG-CoA reductase inhibitors; fibrates; cholesterol absorption inhibitors; HDL cholesterol elevating agents; triglyceride reducing agents; antiageing or antiwrinkle agents; precursor molecules for the generation of hormones; proteins such as collagen and elastin; antibacterial agents; anti acne agents; antioxidants; hair treatments and skin whitening agents; suncreens, sun protectants and filters; variants of human apolipoprotein; precursor molecules for generation of hormones; proteins and peptides thereof; amino acids; plant extracts such as grape seed extract; DHEA; isoflavones; nutritional agents including vitamins, phytosterols and iridoid gylcosides, sesquiterpene lactones, terpenes, phenolic glycosides, triterpenes, hydroquinone derivatives, phenylalkanones; antioxidants such as retinol and other retinoids including retinoic acid and co enzyme Q10; omega-3-fatty acids; glucosamine; nucleic acids, oligonucleotides, antisense pharmaceuticals; enzymes; cytokines; cytokine analogues; cytokine agonists; cytokine antagonists; immunoglobulins; antibodies; antibody pharmaceuticals; gene therapies; lipoproteins; erythropoietin; vaccines; small and large molecule therapeutic agents for the treatment, or prevention of human and animal diseases such as allergy/asthma, arthritis, cancer, diabetes, growth impairment, cardiovascular diseases, inflammation, immunological disorders, baldness, pain, ophthalmological diseases, epilepsy, gynaecological disorders, CNS diseases, viral infections, bacterial infections, parasitic infections, GI diseases, obesity, and haemological diseases.

Some specific non-limiting examples of suitable biologically active compounds include:

Anaesthetics:
 including amino-ester and amino-amide anaesthetics such as benzocaine, chloroprocaine, cocaine, reserpine, guanethidine, cyclomethycaine, dimethocaine/larocaine, propoxycaine, procaine/novocaine, proparacaine, tetracaine/amethocaine; articaine, bupivacaine, carticaine, cinchocaine/dibucaine, etidocaine, levobupivacaine, lidocaine/lignocaine, mepivacaine, piperocaine, prilocalne, ropivacaine, trimecaine, propofol, halothane, enflurane barbiturates, benzodiazepines, neostigmine and ketamine Alkylating Agents:
 including carmustine, cyclophosphamide, ifosfamide, streptozotocin and mechlorethamine Calcium Channel Blockers:
 including amlodipine, aranidipine, azelnidipine, barnidipine, benidipine, cilnidipine, clevidipine, cronidipine, darodipine, dexniguldipine, efonidipine, elnadipine, elgodipine, felodipine, flordipine, furnidipine, iganidipine, isradipine, lacidipine, lemildipine, lercanidipine, manidipine, mesuldipine, nicardipine, nifedipine, niludipine, nilvadipine, nimodipine, nisoldipine, nitrendipine, olradipine, oxodipine, palonidipine, pranidipine, sagandipine, sornidipine, teludipine, tiamdipine, trombodipine, watanidipine, verapamil, gallopamil, benzothiazepine, diltiazem, mibefradil, bepridil, fluspirilene and fendiline Antiarrhythmic and Antiangina Agents:
 including amiodarone, disopyramide, flecamide acetate, quinidine sulphate, nitroglycerine, ranolazine, amiodarone, isosorbide and alteplase Antibacterial, Antibiotic and Antiacne Agents:
 including amoxicillin, ampicillin, azithromycin, benethamine penicillin, bleomycin, benzoyl peroxide, cinoxacin, chloramphenicol, daunorubicin, plicamycin, fluoroquinolones, ciprofloxacin, clarithromycin, clindamycin, clindesse, clofazimine, chlorohexidine gluconate, cloxacillin, demeclocycline, doxycycline, erythromycin, ethionamide, imipenem, indomethacin, lymocycline, minocycline, nalidixic acid, nitrofurantoin, penicillin, rifampicin, spiramycin, sodium sulfacetamide, sulphabenzamide, sulphadoxine, sulphamerazine, sulphacetamide, sulphadiazine, sulphafurazole, sulphamethoxazole, sulphapyridine, tetracycline, cephalexin, cefdinir, triclosan, ofloxacin, vancocin, glyburide, mupirocin, cefprozil, cefuroxime axetil, norfloxacin, isoniazid, lupulone, D-penicillamine, levofloxacin, gatifoxacin, and trimethoprim Anticancer:
 including doxorubicin, 6-thioguanine, paclitaxel, docetaxel, camptothecin, megestrol acetate, navelbine, cytarabine, fludarabine, 6-mercaptopurine, 5-fluorouracil, teniposide, vinblastine, vincristine, cisplatin, colchicine, carboplatin, procarbazine and etopside Antidepressants, Antipsychotics and Antianxiety:
 including alprazolam, amoxapine, bentazepam, bromazepam, clorazipine, clobazam, clotiazepam, diazepam, lorazepam, flunitrazepam, flurazepam, lormetazepam, medazepam, nitrazepam, oxazepam, temazepam, maprotiline, mianserin, nortriptyline, risperidone, sertraline, trazodone, baloperidol, trimipramine maleate fluoxetine, ondansetron, midazolam, chlorpromazine, haloperidol, triazolam, clozapine, fluopromazine, fluphenazine decanoate, fluanisone, perphenazine, pimozide, prochlorperazine, sulpiride, thioridazine, paroxitine, citalopram, bupropion, phenelzine, olanzapine, divalproex sodium and venlafaxine Tricyclics:
 including azothiopine, amitriptyline, famotidine, promethazine, paroxatine, oxcarbazepine and mertazapine Antidiabetics:
  including acetohexamide, chlorpropamide, glibenclaraide, gliclazide, glipizide, metformin, tolazamide, glyburide, glimepiride and tolbutamide Antiepileptics:
  including beclamide, carbamazepine, gapapentin, tiagabine, vigabatrin, topiramate, clonazepam, ethotoin, methoin, methsuximide, methylphenobarbitone, oxcarbazepine, paramethadione, phenacemide, phenobarbitone, phenyloin, phensuximide, primidone, sulthiamine, phenyloin sodium, nirofurantoin monohydrate, gabapentin, lamotrigine, zonisamide, ethosuximide and valproic acid Hypnotics/Sedatives and Muscle Relaxants:
  including zolpidem tartrate, amylobarbitone, barbitone, butobarbitone, pentobarbitone, brotizolam, carbromal, chlordiazepoxide, chlormethiazole, ethinamate, meprobamate, methaqualome, cyclobenzaprene, cyclobenzaprine, tizanidine, baclofen, butalbital, zopiclone, atracurium, tubocurarine and Phenobarbital Antifungal, Antiprotazoal and Antiparasitic Agents:
  including amphotericin, butoconazole nitrate, clotrimazole, econazole nitrate, fluconazole, flucytosine, griseofulvin, itraconazole, ketoconazole, miconazole, natamycin, nystatin, sulconazole nitrate, terconazole, tioconazole and undecenoic acid; benznidazole, clioquinol, decoquinate, diiodohydroxyquinoline, diloxanide furoate, dinitolmide, furzolidone, metronidazole, nimorazole, nitrofurazone, ornidazole, terbinafine, clotrimazole, chloroquine, mefloquine, itraconazole, pyrimethamine, praziquantel, quinacrine, mebendazole and timidazole Antihypertensive and Cardiac Therapeutic Agents:
  including candesartan, hydralazine, clonidine, triamterene, felodipine, gemfibrozil, fenofibrate, nifedical, prazosin, mecamylamine, doxazosin, dobutamine and cilexetil Antimigraine Agents:
  including dihydroergotamine mesylate, ergotamine tartrate, methysergide maleate, pizotifen maleate and sumatriptan succinate Antimuscarinic Agents:
  including atropine, benzhexyl, biperiden, ethopropazine, hyoscyamine, mepenzolate bromide, oxybutynin, oxyphencylcimine and tropicamide Antineoplastic Agents (or Immunosuppressants):
  including aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine, tamoxifen citrate, testolactone, tacrolimus, mercaptopurine and sirolimus Antiparkinsonian Agents:
  including bromocriptine mesylate, levodopa, tolcapone, ropinirole, bromocriptine, hypoglycaemic agents such as sulfonylureas, biguanides, α-glucosidase inhibitors, thaiazolidinediones, cabergoline, carbidopa and lysuride maleate Antithyroid Agents:
  including carbimazole and propylthiouracil Antiviral Drugs:
  including amantadine, retinovir, cidofovir, acyclovir, famciclovir, ribavirin, amprenavir, indinavirm, rimantadine and efavirenz, penciclovir, ganciclovir, vidarabine, abacavir, adefovir, apmrenavir, delavirdine, didanosine, stavudine, zalcitabine, zidovudine, enfuvirtide and interferon Cardiac Inotropic Agents:
  including aminone, milrinone, digitoxin, digoxin, enoximone, lanatoside C and medigoxin Hypo and Hyper Lipidemic Agents:
  including fenofibrate, clofibrate, probucol, ezetimibe and torcetrapib Antiinflammatory:
  including meoxicam, triamcinolone, cromolyn, nedocromil, hydroxychloroquine, montelukast, zileuton, zafirlukast and meloxicam Antihistamine:
  including fexofenadine, chloral hydrate, hydroxyzine, promethazine, cetirazine, cimetidine, clyclizine, meclizine, dimenhydrinate, loratadine, nizatadine and promethazine Antiulcer:
  including omeprazole, lansoprazole, pantoprazole and ranitidine Diuretics:
  including hydrochlorothiazide, amiloride, acetazolamide, furosemide and torsemide Opioids:
  including natural opiates which are alkaloids contained in the resin of the opium poppy such as morphine, codeine and thebaine; semi-synthetic opioids created from natural opiates such as hydromorphone, hydrocodone, oxycodone, oxymorphone, desomorphine, diacetylmorphine (heroin), nicomorphine, dipropanoylmorphine, benzylmorphine and ethylmorphine; fully synthetic opioids such as fentanyl, pethidine, methadone, tramadol and dextropropoxyphene; and, endogenous opioid peptides, produced naturally in the body, such as endorphins, enkephalins, dynorphins, and endomorphins; opioid analgesics including opioid receptor agonists, opioid receptor partial agonists, opioid antagonist or opioid receptor mixed agonist-antagonists; opioid receptor agonists including morphine, depomorphine, etorphine, heroin, hydromorphone, oxymorphone, levorphanol, methadone, levomethadyl, meperidine, fentanyl, sufentanyl, alfentanil, codeine, hydrocodone, oxycodone, and mixtures of the foregoing; opioid receptor antagonists including naloxone and naltrexone; opioid receptor mixed agonist-antagonist which has mixed opioid agonist/antagonist activities, or one that exhibits only partial agonist activity, including buprenorphine, nalbuphine, butorphanol, pentazocine, and mixtures of such compounds; opioids which exhibit partial agonist activity, including ethylketocyclazocine; opium alkaloids including phenanthrenes which are naturally occurring in opium such as codeine, morphine, thebaine and oripavine (the active metabolite of thebaine); synthetic derivatives such as diacetylmorphine (heroin), dihydrocodeine, hydrocodone, hydromorphone, nicomorphine, desmorphine, ethylmorphine, dipropanoylmorphine, oxycodone and oxymorphone; synthetic opioids including anilidopiperidines such as fentanyl, alphamethylfentanyl, alfentanil, sufentanil, remifentanil, carfentanyl and ohmefentanyl, Phenylpiperidines such as pethidine (meperidine), ketobemidone, MPPP, allylprodine, prodine and PEPAP; diphenylpropylamine derivatives such as propoxyphene, dextropropoxyphene, dextromoramide, bezitramide, piritramide, methadone, dipipanone, levomethadyl acetate (LAAM), difenoxin, diphenoxylate and loperamide; benzomorphan derivatives such as dezocine, pentazocine and phenazocine; oripavine derivatives such as buprenorphine, dihydroetorphine and etorphine; morphinan derivatives such as butorphanol, nalbuphine, levorphanol and levomethorphan, and others such as lefetamine, meptazinol, tilidine, tramadol and tapentadol; opioid receptor antagonists including nalmefene, naloxone and naltrexone NSAIDs:
including arylalkanoic acid sub-group of class which includes diclofenac, aceclofenac, acemetacin, alclofenac, bromfenac, etodolac, indometacin, indometacin farnesil, nabumetone, oxametacin, proglumetacin, sulindac and tolmetin; 2-arylpropionic acid (profens) sub-group of class which includes alminoprofen, benoxaprofen, carprofen, dexibuprofen, dexketoprofen, fenbufen, fenoprofen, flunoxaprofen, flurbiprofen, ibuprofen, ibuproxam, indoprofen, ketoprofen, ketorolac, loxoprofen, miroprofen, naproxen, oxaprozin, pirprofen, suprofen, tarenflurbil and tiaprofenic acid; and N-arylanthranilic acid (fenamic acid) sub-group of class which includes flufenamic acid, meclofenamic acid, mefenamic acid and tolfenamic acid; tromethamine, celecoxib, nepafenac, aspirin, rofecoxib, naproxen, sulindac, piroxicam, pheylbutazone, tolmetin, indomethacin, acetominophen (paracetamol), tramadol and propoxyphene Retinoids:
including first generation retinoids such as retinol, retinal, tretinoin (retinoic acid, Retin-A), isotretinoin and alitretinoin; second generation retinoids such as etretinate and its metabolite acitretin; third generation retinoids such as tazarotene, bexarotene and adapalene Hormones and Steroids:
including adrenocorticotrophic hormone (ACTH), antidiruetic hormone (vasopressin), atrial-nartreuretic factor (ANF), atrial-nartreuretic peptide (ANP), beclomethasone, cortisone, scopolamine, dopamine, epinephrine, catecholamines, cholecystokinin, clomiphene citrate, danazol, dexamethasone, diethylstilbestrol (DES), ethinyl estradiol, fludrocortison, finasteride, follicle stimulating hormone, gastrin, hydroxyprogesterone, growth hormone, insulin, leptin, luteinizing hormone, medroxyprogesterone acetate, mestranol, quinestrol, methyltestosterone, nandrolone, norethindrone, norethisterone, norgestrel, estradiol, conjugated oestrogens, oxandrolone, oxytocin, prednisone, progesterone, prolactin, protogalndins, somatostatin, stanozolol, stibestrol, thyroxine, prednisolone phosphate, triamcinolone, mifepristone acetonide, budesonide, levothyroxine, testosterone, testosterone cypionate, fluoxymesterone, flutamide, mometasone furoate, cyproterone, fluoromethalone, goserelin, leuprolide, calcitonin, halobetasol, hydrocortisol and tibolone Statins and Derivatives:
including atorvastatin, fluvastatin, lovastatin, nystatin, rosuvastatin, pravastatin, orlistat and simvastatin Stimulants: including amphetamine, phentermine, tyramine, ephedrine, metaraminol, phenylephrine, dexamphetamine, dexfenfluramine, fenfluramine, nicotine, caffeine and mazindol Vasocontrictors:
including desmopressin Vasodilitors:
including carvedilol, terazosin, phentolamine and menthol Antialzheimers:
including levetiracetam, levitiracetam and donepezil ACE Inhibitors:
including benzapril, enalapril, ramipril, fosinopril sodium, lisinopril, minoxidil, isosorbide, rampril and quinapril Beta Adrenoreceptor Antagonists:
including atenolol, timolol, pindolol, propanolol hydrochloride, bisoprolol, esmolol, metoprolol succinate, metoprolol and metoprolol tartrate Angiotensin II Antagonists:
including losartan Platelet Inhibitors:
including abciximab, clopidrogel, tirofiban and aspirin Alcohols and Phenols:
including tramadol, tramadol hydrochloride, allopurinol, calcitriol, cilostazol, soltalol, urasodiol bromperidol, droperidol, flupenthixol decanoate, albuterol, albuterol sulphate, carisoprodol, chlobetasol, ropinirol, labetalol, and methocarbamol Ketones and Esters:
including amioderone, fluticasone, spironolactone, prednisone, triazodone, desoximetasone, methyl prednisdone, benzonatate nabumetone and buspirone Antiemetics:
including metoclopramide Ocular Treatments:
including dorzolamide, brimonidine, olopatadine, cyclopentolate, pilocarpine and echothiophate Anticoagulant and Antithrombitic Agents:
including warfarin, enoxaparin and lepirudin Treatments for Gout:
including probenecid and sulfinpyrazone COPD and Asthma Treatments:
including ipratropium Treatments for Osteoporosis:
including raloxifene, pamidronate and risedronate Cosmetic Peptides:
including acetyl hexapeptide-3, acetyl hexapeptide-8, acetyl octapeptide and I-carnosine vaccines:
including vaccines comprising toxoids (inactivated toxic compounds); proteins, protein subunits and polypeptides; polynucleotides such as DNA and RNA; conjugates; adjuvants such as saponins, virosomes, inorganic and organic adjuvants, for example zostavax Nutraceutical and Cosmeceutical Actives:
including coenzyme $Q_{10}$ (or ubiquinone), ubiquinol or resveratrol; a carotenoid such as $\alpha$, $\beta$, or $\gamma$-carotene, lycopene, lutein, zeaxanthin and astaxanthin; a phytonutrient, such as lycopene, lutein and seaxanthin; an unsaturated fatty acid such as linoleic acid, conjugated linoleic acid, linolenic acid, omega-3 fatty acids including but not limited to docosahexaenoic acid (DHA) and eicosapentaeonic acid (EPA) and their glycerol-esters; fat-soluble vitamins including vitamin D (D2, D3 and their derivatives), vitamin E ($\alpha$, $\beta$, $\gamma$, $\delta$-tocopherols, or $\alpha$, $\beta$, $\gamma$, $\delta$-tocotrienols), vitamin A (retinol, retinal, retinoic acid and derivatives), vitamin K ($K_1$, $K_2$, $K_3$ and their derivatives) capric/caprylic triglycerides, folic acid, iron, niacin, glyceryl linoleate, omega 6 fatty acids, vitamin F, selenium, cyanocobalamin, aloe vera, beta glucan, bisabolol, camellia thea (green tea) extract, capric/caprylic triglycerides, centella asiatica (gotu cola) extract, cetearyl olivate, chlorophyll, citrus sinensis (orange) oil, cocoyl proline, dicapryl ether, disodium lauriminodipropionate tocopheryl phosphates (vitamin E phosphates), glycerin, glyceryl oleate, *glycyrrhiza glabra* (licorice) root extract, hamamelis virgiana (witch hazel) extract, lactic acid, lecithin, lutein, *macadamia integrifolia* (macadamia) seed oil, *matricaria chamomilla* (chamomile) extract, *oenothera biennis* (evening primrose) oil, *olea europaea* (olive) leaf extract, rice bran oil, *persea gratissima* (avocado) oil, *polygonum multiflorum* extract, pomegranate sterols, resveratrol, *rosa eglanteria* (rose hip) oil, *santalum spicatum* (sandalwood) oil, titanium dioxide, folic acid, glycerin, glyceryl linoleate (omega 6 fatty acids vitamin F), vitamin A palmitate, *vitis vinifera* (grapeseed) oil, halobetasol, adenosine, adenosine triphosphate, alpha hydroxy acid, allantoin, hyaluronic acid and derivatives, isolutrol, tranexamic acid, glycolic acid, arginine, ascorbyl glucosamine, ascorbyl palmitate, salicylic acid, carnosic acid, alpha lipoic acid, gamma linolenic acid (GLA), panthenol, retinyl propionate, retinyl pamitate, furfuryladenine, retinaldehyde, copper pepetides, idebenone, dimethylaminoethanol (DMAE), niacinamide, beta-glucan, palmitoyl pentapeptide-4, palmitoyl oligopeptide/tetrapetide-7, ethocyn, ceramides, phenylalanine, glucuronolactone, L-carnitine, hydroxylapetite, palmitoyl tripetide-3, forskolin, zinc oxide, α-bisabolol, eugenol, silybin, soy isoflavones, aucubin, catalpol, pseudoguaianolide from *Arnica chamissonis*, rosmarinic acid, rosmanol, salicylates for example salicin, saligenin and salicyclic acid, taxasterol, α-lactucerol, isolactucerol, taraxacoside, ceremides, arbutin, gingerols, shagaols, hypercin, elastin, collagen and peptides thereof.

Particularly preferred biologically active compounds include alprazolam, donepazil, rispiredone, lorazepam, nicotine, lidocaine, diclofenac, felodipine, insulin, ketoralac, prilocalne, halobetasol, hydrocortisol, opioids such as oxycodone or dihydrohydroxycodeinone (oxycodone base).

It is to be understood that pharmaceutically, nutraceutically or cosmeceutically acceptable derivatives of biologically active compounds are included within the scope of the present invention.

The term "pharmaceutically, nutraceutically or cosmeceutically acceptable derivatives" includes, but is not limited to, pharmaceutically, nutraceutically or cosmeceutically acceptable salts, esters, salts of such esters, ethers, or any other derivative including prodrugs and metabolites, which upon administration to a subject (e.g. patient, human or animal) in need is capable of providing, directly or indirectly, a biologically active compound as otherwise described herein.

As used herein, the term "pharmaceutically, nutraceutically or cosmeceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically, nutraceutically or cosmeceutically acceptable salts are well known in the art. For example, S. M. Berge, et al. describe pharmaceutically, nutraceutically or cosmeceutically acceptable salts in detail in J. Pharmaceutical Sciences, 66:1-19, 1977. Examples of pharmaceutically, nutraceutically or cosmeceutically acceptable nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate, and aryl sulfonate.

The term "pharmaceutically, nutraceutically or cosmeceutically acceptable ester" refers to esters which are hydrolysed in vivo and include those that break down readily in the human body to leave the parent compound or a salt thereof. Suitable ester groups include, for example, those derived from pharmaceutically, nutraceutically or cosmeceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically, nutraceutically or cosmeceutically acceptable prodrugs" as used herein refers to those prodrugs of the biologically active compounds which are, within the scope of sound medical judgment, suitable for use in contact with the tissues of a subject with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987.

The present invention is further not limited solely to the administration of one biologically active compound: more than one biologically active compound or other therapeutic compounds may be incorporated into the composition, or matrix layer.

The biologically active compound may be present in a therapeutically effective amount, that is, an amount necessary to achieve a desired therapeutic effect. Typically, the biologically active compound will be present in an amount within the range of about 0.1% w/w to about 30% w/w, within the range of about 0.1% w/w to about 20% w/w, within the range of about 0.1% w/w to about 10% w/w, of the total concentration of the composition, or matrix layer. In one embodiment, the matrix layer will have a biologically active compound concentration within the range of about 3.0% w/w to about 15.0% w/w of the total concentration of the composition, or matrix layer.

The ratio of biologically active compound:TP (% w/w) may be within the range of about 5:5 to about 5:0.5, with the most preferred value preferably being about 5:1. The polymer carrier:[biologically active compound and TP] may be within the range of about 1:1 to about 3:1, with preferred values preferably being within the range of about 7:6 to about 7:3.

Preparation of the Transdermal Delivery Patch

The composition, or matrix layer, may form part of a transdermal delivery matrix patch. The transdermal delivery patch may be prepared by a variety of techniques.

One technique involves combining the polymer carrier and any inert carrier components such as an anti-tacking agent and/or plasticizer with a suitable solvent (e.g. 50% water, 50% ethanol). This is combined with a dispersion comprising the biologically active compound and the mixture of a mono-tocopheryl phosphate compound and a di-tocopheryl phosphate compound, and is stirred until complete homogenisation is achieved. In one embodiment, the composition may then be placed in a suitable mould and dried. In a preferred method, the composition may be dried by heating up to about 90° C., preferably for 0.5 to 24 hours. However, formulating and/or drying may be conducted at a temperature within the range of about 30° C. to about 90° C. It has been found that formulating and/or drying at a temperature of about 75° C. results in better delivery of the biologically active compound. In an alternate embodiment, the composition may be cast on a surface (e.g. a roller) and then dried under heat.

The composition comprising a mixture of a mono-tocopheryl phosphate compound and a di-tocopheryl phosphate compound and a polymer carrier is suitable for use as a matrix layer. The matrix layer may be a solid or semi-solid layer.

The transdermal delivery patch usually would also comprise a backing layer. The backing layer acts as a support or substrate for the composition, or matrix layer. When preparing a transdermal delivery patch using a mould, the backing layer would be placed in the mould before addition of the composition, or matrix layer.

Accordingly, the composition, or matrix layer, essentially has two surfaces: a first surface and a second surface opposite the first surface, where the first surface is in contact with the backing layer and the second surface being adapted to be in diffusional contact with the skin of a subject. The subject may be a human or animal.

Preferably, the backing layer is occlusive or impermeable to protect the composition, or matrix layer, from the outer environment. However, a non-occlusive backing layer could also be used, so long as the packaging of the transdermal delivery patch is fully occlusive to prevent degradation of the composition, or matrix layer. An occlusive backing layer is preferred.

The backing layer may be of any thickness, however in the art, backing layers typically have a thickness of about 0.0005 inches to about 0.01 inches.

The transdermal delivery patch may further comprise a liner which is a removable protective or impermeable layer, usually but not necessarily rendered "non-stick" so as not to stick to the composition, or matrix layer. The liner, which may also be referred to as the release liner, protects the transdermal delivery patch during storage. During use, the release liner is to be removed.

The liner may be made from the same material as the backing layer, however it may also be a metal foil, Mylar (registered trademark), polyethylene terephthalate, siliconized polyester, fumed silica in silicone rubber, polytetrafluoroethylene, cellophane, siliconized paper, aluminized paper, polyvinyl chloride film, composite foils or films containing polyester such as polyester terephthalate, polyester or aluminized polyester, polytetrafluoroethylene, polyether block amide copolymers, polyethylene methyl methacrylate block copolymers, polyurethanes, polyvinylidene chloride, nylon, silicone elastomers, rubber-based polyisobutylene, styrene, styrene-butadiene, and styrene-isoprene copolymers, polyethylene, and polypropylene.

The release liner may be of any thickness, however in the art, release liners typically have a thickness of about 0.01 mm to about 2 mm.

The transdermal delivery patch may also comprise an adhesive layer. The adhesive layer may be an additional layer to the composition, or matrix layer, or may be included on the outer margin of the backing layer where the backing layer extends beyond the edges of the composition, or matrix layer. Polymeric adhesives useful for transdermal patches include polyacrylate polymers, rubber-based adhesives and polysiloxane adhesives. These types of materials, as well as others, are described by Van Norstrand (The Handbook of Pressure Sensitive Adhesive Technology Second Edition 1989), which is hereby incorporated by reference. Examples of commercially available adhesives include, but are not limited to, polyacrylate adhesives sold under the trademarks DURO-TAK (registered trademark) by National Starch and Chemical Corporation, Bridgewater, N.J., as well as GELVA-MULTI-POLYMER SOLUTION (registered trademark) by Cytek Surface Specialties, Smyrna, Ga.

Advantages

It has surprisingly been found that biologically active compounds can be effectively administered using a transdermal delivery patch comprising a composition, or matrix layer, which comprises a mixture of a mono-tocopheryl phosphate compound and a di-tocopheryl phosphate compound and a polymer carrier.

Transdermal delivery options for include, for example, topical creams and gels, and skin patches.

Creams and gels may present difficulties with compliance and dosage control, and may be considered messy or unpleasant by patients.

There are different forms of skin patches, including "reservoir" patches and "matrix" patches. Patches may also be single- or multi-layered. A "reservoir" patch essentially has a liquid or gel compartment containing the drug solution or suspension separated by a membrane and a layer of adhesive. In a "matrix" patch, the drug dispersion is present in a semi-solid or solid layer, which may or may not also comprise the adhesive material.

Reservoir patches overcome some of the dosage difficulties with topical creams and gels, however the delivery may be uneven or inconsistent, and there is some risk of perforation of the reservoir. An additional issue relates to delivery of prescribed drugs which may be addictive and subject to abuse. Gels, creams and reservoir patches provide limited barriers to extraction of the drug substance, whereas incorporation of the drug substance within a composition, or matrix layer, represents a significant, if not almost impossible barrier to extraction of the drug substance.

Delivery of an active orally or by injection typically results in a delivery profile which is non-linear. Transdermal delivery provides a non-invasive way of potentially achieving sustained steady state delivery.

Without wishing to be bound by theory, the presence of a mixture of a mono-tocopheryl phosphate compound and a di-tocopheryl phosphate compound is considered to enhance the skin permeation of the biologically active compound. It has also been found that the components of the composition, or matrix layer, do not formulate well together without the presence of a mixture of a mono-tocopheryl phosphate compound and a di-tocopheryl phosphate compound. It has also been found that the presence of a phosphate compound of tocopherol will act to reduce skin irritation caused by many the biologically active compounds.

FIGURES

The examples will be described with reference to the accompanying figures in which.

EXAMPLES

Various embodiments/aspects of the present invention will now be described with reference to the following non-limiting examples.

Example 1

Manufacture of Transdermal Delivery Patch

| Final composition, or matrix layer | |
|---|---|
| Components | Percentage by weight, after drying |
| A combination of mono-(tocopheryl) phosphate and di-(tocopheryl) phosphate in a ratio of 6:4 | 1.1% w/w |
| Oxycodone | 5.5% w/w |
| Eudragit E100 (polymethyl methacrylate) | 60.6% w/w |
| Dibutyl sebacate | 27.3% w/w |
| Succinic acid | 5.5% w/w |

Small Scale Laboratory Manufacturing

The components were dissolved in a solvent solution (acetone:isopropanol:ethyl alcohol 60:6.6:33.5 by % weight). The resulting solution was then poured into individual casts (containing suitable backing layers) at room temperature and the solvent was allowed to evaporate at 75° C. for 1.5 hours.

Large Scale Manufacturing

All composition, or matrix layer, components could be combined at a suitable temperature to produce a homogeneous molten mass. The molten mass can then be cast on a cold surface (for example, a rotating mill with a suitable backing layer, or sheet, thereon) and allowed to solidify. Individual transdermal delivery patches of varying sizes may then be cut.

Figure 1:
FIG. 1 is a schematic diagram of a transdermal delivery patch of one embodiment of the present invention.

In both methods, the composition, or matrix layer, would be relatively thin; however, the thickness of the composition, or matrix layer, can be varied depending on the desired properties of the transdermal delivery patch. FIG. 1 shows an example of a transdermal delivery patch of one embodiment of the present invention.

Example 2

Alternate Method for Manufacture of Transdermal Delivery Patch transdermal delivery patches were constructed by dissolving 20% w/w solid mixture of Eudragit E100 granules, dibutyl sebacate, succinic acid (the components other than TPM and oxycodone in the composition, or matrix layer, may collectively be referred to as the "polymer carrier"); a combination of mono-(tocopheryl)phosphate and di-(tocopheryl) phosphate in a ratio of 6:4 (TPM); and oxycodone base in 60:6.6:33.4 acetone/isopropyl alcohol/ethyl alcohol. The mixture was then transferred into 6 cm² circular aluminium cast-lined on the underside with polyester backing (1.66 mil, 3M Scotchpak™, 3M, MN) and the solvent evaporated in an oven at either 45° C. overnight or 75° C. for 1.5 hours. Where glue was used, the glue was DuroTak adhesive and in this example succinic acid was omitted from the formulation.

TABLE

Composition, excipient ratios and manufacture conditions of transdermal delivery patches

| Patch | Ratio (PC:O:TPM)* | Oxycodone (mg) | Vol. stock (ml) | Dry temp./ time | Succinic acid | Glue |
|---|---|---|---|---|---|---|
| 1 | 10:5:1 | 10 | 2 | 45° C. overnight | Yes | No |
| 2 | 14:5:1 | 10 | 2 | 45° C./overnight | Yes | No |
| 3 | 14:5:1 | 5 | 1 | 45° C./overnight | Yes | No |
| 4 | 14:5:1 | 5 | 1 | 75° C./1.5 h | Yes | No |
| 5 | 14:10:2 | 5 | 0.5 | 75° C./1.5 h | No | Yes |

*Refers to ratio of polymer carrier:oxycodone:TPM

Example 3

Comparative Testing for Drying Temperatures

Oxycodone transdermal delivery patches were made according to Example 1 (small scale), testing the variable of the two different heating regimes. The transdermal delivery patches were adhered to full thickness human skin applied to a Franz cell with PBS as the receiver solution. Time points were taken at 18, 22, 24, 42, 44, 68 and 75 hours and the receiver solution was tested by HPLC to determine the concentration of oxycodone which had passed through the skin.

TABLE

Parameters in the patches tested

| Patch | Ratio (PC:O:TPM)* | Oxycodone (mg) | Vol. stock (ml) | Dry temp./ time | Succinic acid | Glue |
|---|---|---|---|---|---|---|
| A | 14:5:1 | 10 | 2 | 45° C./overnight | Yes | No |
| B | 14:5:1 | 10 | 2 | 75° C./1.5 h | Yes | No |

*Refers to ratio of polymer carrier:oxycodone:TPM

Figure 2:
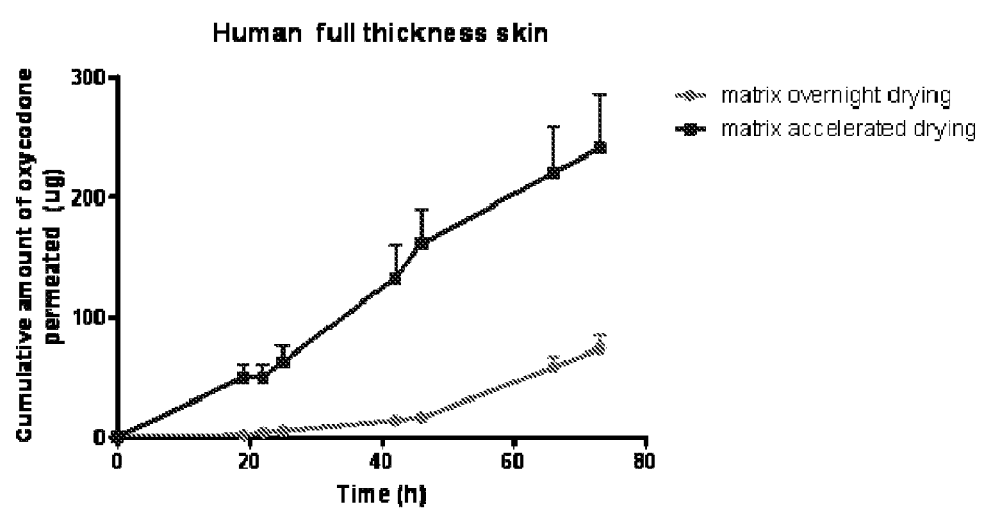
FIG. 2 is a graph comparing the delivery of oxycodone using a transdermal delivery patches of the present invention prepared with different drying regimes.

The results outline in FIG. 2 show that the transdermal delivery patch manufactured using the higher (accelerated) drying temperature has increased transdermal delivery properties compared with the transdermal delivery patch manufactured with drying at a lower temperature.

Example 4

Comparative Testing to Determine Effect of an External Glue Layer

Transdermal delivery patches were manufactured and the receiver solution tested as in Example 3, with testing time points of 0.5, 1, 3, 4 and 20 hours.

TABLE

Parameters in the patches tested

| Patch | Ratio (PC:O:TPM)* | Oxycodone (mg) | Vol. stock (ml) | Dry temp./time | Succinic acid | Glue |
|---|---|---|---|---|---|---|
| C | 14:5:1 | 10 | 2 | 75° C./1.5 h | Yes | No |
| D | 14:5:1 | 10 | 2 | 75° C./1.5 h | No | Yes |

*Refers to ratio of polymer carrier:oxycodone:TPM

Figure 3:
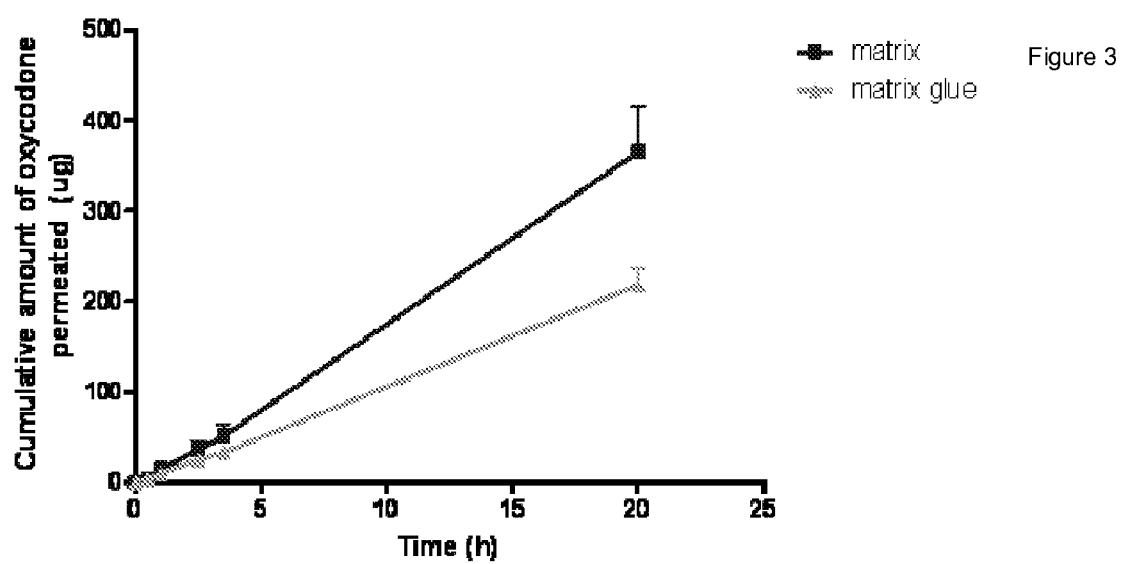
FIG. 3 is a graph comparing the delivery of oxycodone using transdermal delivery patches of the present invention prepared with and without a glue layer.

The results of this comparison outlined in FIG. 3 clearly demonstrate that using a transdermal delivery patch which includes an adhesive layer results in reduced transdermal penetration of the oxycodone compared with the transdermal delivery patches formulated to be self-adhesive.

Example 5

Comparative Testing to Determine Effect of an Occlusive Backing Layer Compared with No Backing Layer The transdermal delivery patches were manufactured and the receiver solution tested as in Examples 3 and 4, at time points 1, 2, 3, 4 and 5 hours.

TABLE

Parameters in the patches tested

| Patch | Ratio (PC:O:TPM)* | Oxycodone (mg) | Vol. stock (ml) | Dry temp./time | Occlusive backing | Glue |
|---|---|---|---|---|---|---|
| E | 14:5:1 | 10 | 2 | 75° C./1.5 h | Yes | No |
| F | 14:5:1 | 10 | 2 | 75° C./1.5 h | No | No |

*Refers to ratio of polymer carrier:oxycodone:TPM

Figure 4:
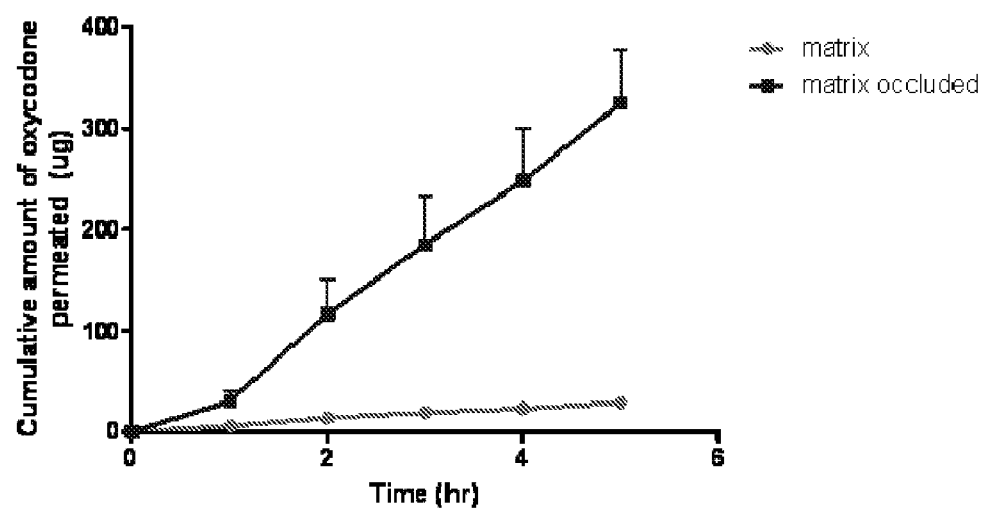
FIG. 4 is a graph comparing the delivery of oxycodone using transdermal delivery patches of the present invention prepared with and without an occlusive backing layer.

The results outlined in FIG. 4 clearly show that penetration of the oxycodone transdermally is far superior when an occlusive backing layer is used with the patch compared with a patch without the adhesive backing layer.

Example 6

Pharmacokinetic Testing

This example compares plasma PK parameters using Patch Nos. 1, 2, 4 and 5 from Example 2.

Transdermal delivery patches were cut from the polyester backing and adhered to the shaved and washed back of a 10-12 week old male Sprague-Dawley rat with a 6×7 cm Tegaderm HP™ (3M, MN) adhesive dressing either with the backing layer in place or removed (see Table below). Tegaderm serves to hold the occlusive backing layer in place, or if the backing layer is absent, holds the transdermal delivery patch itself in place.

The day after the transdermal delivery patches were adhered to the shaved section, blood samples removed from the tail tip following ~1 mm tip amputation at specified times. The PK parameters quantified were:

$C_{max}$: the maximal observed plasma oxycodone concentration.

$AUC_{0-4}$: The area under the curve between 0 and 4 hours (the duration of the experiment was 4 hours) and is a measure of the total amount of drug delivered.

Figure 5:
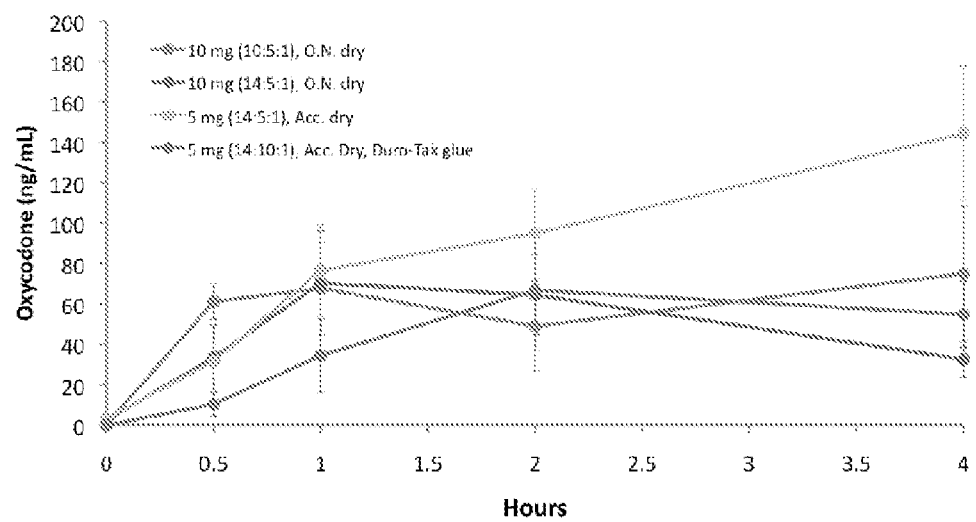
FIG. 5 is a graph showing the results of pharmacokinetic testing conducted after application of transdermal delivery patches of the present invention.

The results in FIG. 5 and Table below demonstrate that the transdermal delivery patches of the present invention in various formulations are able to effectively deliver the oxycodone to the rats as demonstrated by the pharmacokinetic data.

TABLE

Estimated pharmacokinetic parameters of rats administered transdermal delivery patches

| Patch | Oxycodone dose (mg/kg) | Occlusive | n | $C_{max}$ (ng/mL) | $AUC_{0-4}$ (ng · mL/min) |
|---|---|---|---|---|---|
| 1 | 41.8 ± 0.4 | No | 17 | 93 ± 16 | 13681 ± 2367 |
| 2 | 45.0 ± 2.1 | Yes | 9 | 92 ± 27 | 11959 ± 2910 |
| 4 | 21.7 ± 0.1 | Yes | 5 | 144 ± 33 | 21637 ± 5189 |
| 5 | 18.1 ± 0.3 | Yes | 5 | 74 ± 29 | 11161 ± 4636 |

'n' = no. of animals

Example 7

Pharmacodynamic Testing

Rats were prepared and dosed similar to Example 6 using Patch Nos. 1, 3 and 5 from Example 2.

The day after the transdermal delivery patches were adhered to the shaved section, antinociception of the hindpaw was assessed with a plantar analgesiometer with the IR source calibrated to 190 Mu/cm².

The following PD parameters were assessed:

Maximum: The maximum time it took for the rat to remove its paw in response to the heat stimulus. The higher the number, the longer it took for the rat to respond and the deeper the oxycodone induced analgesia.

AUC: This is a measure of the total analgesia over the observation period as measured by the area under the curve between 0 and 4 hour, and is useful for comparing the response to different treatments.

Figure 6:
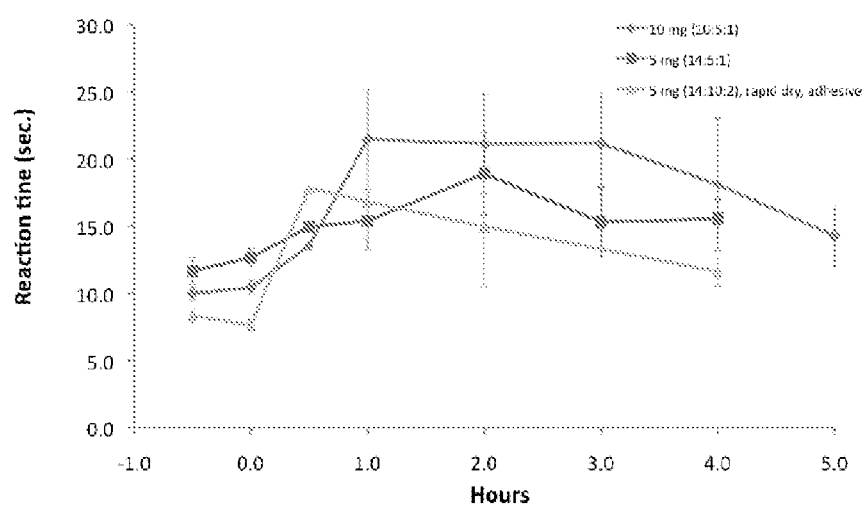
FIG. 6 is a graph showing the results of pharmacodynamic testing conducted after application of transdermal delivery patches of the present invention.

The baseline response time is indicated in FIG. 6 at t=(−0.5 h) and t=0.

The results outlined in the Table below and FIG. 6 demonstrate that analgesia was effectively administered to the rats using a variety of compositions of the present invention.

TABLE

Pharmacodynamic parameters from rats administered different transdermal delivery patches

| Patch | Oxycodone dose (mg/kg) | n | Max (sec.) | $AUC_{0-4}$ (sec/h) |
|---|---|---|---|---|
| 1 | 41.0 ± 0.8 | 5 | 20.7 ± 3.5 | 57.6 ± 9.1 |
| 3 | 21.8 ± 0.6 | 5 | 22.3 ± 3.3 | 76.8 ± 13.1 |
| 5 | 21.6 ± 0.5 | 4 | 20.5 ± 2.3 | 64.0 ± 6.4 |

'n' = no. of animals

Example 8

Alternate Plasticisers

The following formulations were prepared as outlined in Example 2. Formulation 1 was cast onto a die and Formulation 2 was cast onto a plate. The percentages below reflect the composition when the patch is dry.

| Formulation 1 ( 1% T80, dbs) | % w/w |
|---|---|
| Eudragit 100 | 60.59 |
| DBS | 26.28 |
| Succinic acid | 5.46 |
| Oxycodone | 5.56 |
| Tocopheryl phosphate | 0.67 |
| Di-tocopheryl phosphate | 0.44 |
| Tween 80 | 1.00 |
| | 100.00 |

| Formulation 2 (3% ML, 25% T) | % w/w |
|---|---|
| Eudragit 100 | 60.59 |
| Transcutol | 24.28 |
| Succinic acid | 5.46 |
| Oxycodone | 5.56 |
| Tocopheryl phosphate | 0.67 |
| Di-tocopheryl phosphate | 0.44 |
| Methyl laurate | 3.00 |
| | 100.00 |

The transdermal delivery patches were adhered to full thickness human skin applied to a Franz cell with PBS as the receiver solution. Time points were taken at 1, 2, and 4 hours and the receiver solution was tested by HPLC to determine the concentration of oxycodone which had passed through the skin.

Figure 7:
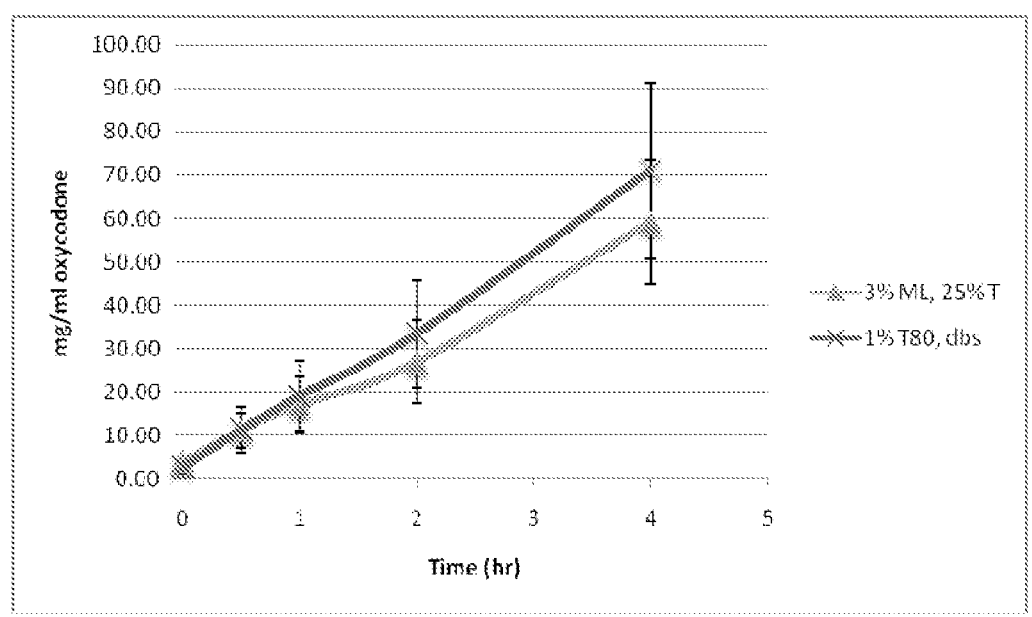
FIG. 7 is a graph comparing the delivery of oxycodone using transdermal delivery patches of the present invention comprising different plasticisers.

The results are outlined in FIG. 7 and demonstrate that delivery of oxycodone can be achieved using alternate plasticisers.

Example 9

Alternate Polymer Carrier

The following formulations were prepared as in Example 1, however with the composition was cast onto a flat surface or plate instead of a die.

| 20% tran, 3% ML, 1% Span | 20% tran, 1% Lau, 1% Span | 20% tran, 1% Span | 3% ML | 1% Span |
|---|---|---|---|---|
| 20% w/w transcutol | 20% w/w transcutol | 20% w/w transcutol | 3% w/w Methyl laurate | 1% w/w Span 80 |
| 3% w/w Methyl laurate | 1% w/w Lauric acid | 1% w/w Span 80 | DuroTak to 100% w/w | DuroTak to 100% w/w |
| 1% w/w Span 80 | 1% w/w Span 80 | DuroTak to 100% w/w | 5.5% w/w Oxycodone | 5.5% w/w Oxycodone |
| DuroTak to 100% w/w | DuroTak to 100% w/w | 5.5% w/w Oxycodone | 1.1% w/w TPM | 1.1% w/w TPM |
| 5.5% w/w Oxycodone | 5.5% w/w Oxycodone | 1.1% w/w TPM | | |
| 1.1% w/w TPM | 1.1% w/w TPM | | | |

The transdermal delivery patches were adhered to full thickness human skin applied to a Franz cell with PBS as the receiver solution. Time points were taken at 1, 2, and 4 hours and the receiver solution was tested by HPLC to determine the concentration of oxycodone which had passed through the skin.

Figure 8:
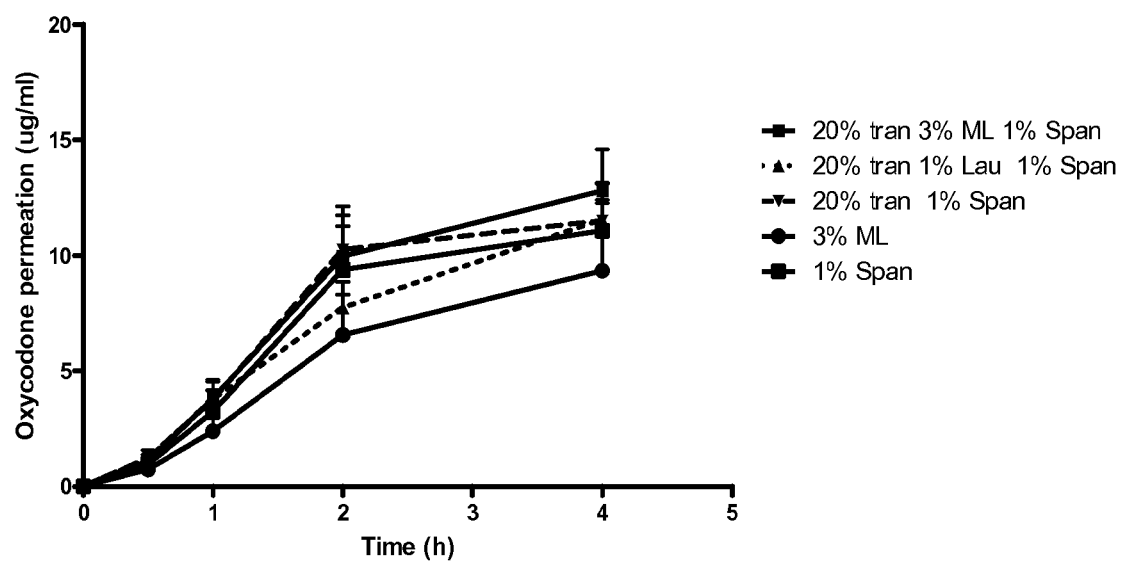
FIG. 8 is a graph comparing the delivery of oxycodone using transdermal delivery patches of the present invention comprising different plasticisers and polymer carriers.

The results are outlined in FIG. 8 and demonstrate that oxycodone can be delivered transdermally using an alternate polymer carrier.

Example 10

Investigation into the Pharmacodynamics of Insulin Formulated into Transdermal Delivery Patches Four transdermal delivery patches of the present invention were tested against a positive control gel.

The table below sets out the composition of the composition, or matrix layer, in each of the four transdermal delivery patches. The polyvinylpyrrolidone was found to provide the composition, or matrix layer, with sufficient "tackiness" to avoid the need to include any inert carrier components. The dry weight of each transdermal delivery patch was 60 mg.

| Patch | TPM | Polyvinylpyrrolidone | Insulin |
|---|---|---|---|
| 1 | 1.2 mg (2% w/w) | 54.8 mg (91.33% w/w) | 4 mg (6.67% w/w) |
| 2 | 0.6 mg (1% w/w) | 55.4 mg (92.33% w/w) | 4 mg (6.67% w/w) |
| 3 | 0.6 mg (1% w/w) | 56.4 mg (94.0% w/w) | 3 mg (5% w/w) |
| 4 | 1.2 mg (2% w/w) | 50.8 mg (84.6% w/w) | 8 mg (13.33% w/w) |

The components of the composition, or matrix layer, were dissolved in a solvent solution (50% water, 50% ethanol). The resulting solution was then poured into individual casts (containing suitable backing layers) at room temperature and the solvent was allowed to evaporate at 75° C. for 1.5 hours.

300 mg of gel was used as the positive control, which comprised 2.25 mg/ml insulin, 2% TPM (2:1), 30% ethanol, 1% carpobol 934 in water adjusted to pH=4.7.

Study Design

The study was a cross-over design to test the effect of transdermal delivery patches of the present invention compared to the gel. In this design, each animal received four of the five treatments across the course of the study. The animals were male and 10-12 weeks of age. Each treatment group was 11 animals. All animals were >300 g in weight, and had circulating glucose concentrations of >10 mmol/L in the fasted state (mean fasted glucose concentration was 21.37±0.85 mmol/L). The key endpoint of the study was blood glucose levels during a 5-hour insulin tolerance test, conducted as described below.

Streptozotocin Administration

Diabetes was induced by the administration of a single intraperitoneal injection of streptozotocin (STZ) 50 mg/kg (Sigma Chemicals) dissolved in sodium citrate buffer (0.1 mol/L, pH 4.5) immediately before use. Rats were considered diabetic and included in the study if their blood glucose was greater than 16 mmol/L 24 hours after the STZ injection. In all groups blood glucose measurements were made by obtaining a spot sample from tail tipping. Animals were left for 5 days following STZ administration prior to testing.

Treatment Application 24 hours before the application of the gel and transdermal delivery patches the animals were anaesthetised and ~30 cm² of fur was shaved from the back, avoiding any damage to the skin that could enhance absorption of the formulations. The gel was applied at a dose of 12 mg/cm² across the shaved area. The transdermal delivery patches were adhered to the shaved area and protected with the application of a tegaderm dressing. The insulin tolerance tests were performed 24 hours after removing the fur. Following each treatment, the animals were allowed to recover for 3 days before the next treatment.

ITT (Insulin Tolerance Test)

Animals were fasted for 2 hours prior to the application of insulin or control formulations. Spot blood samples were taken from the tail at 0, 30, 60, 90, 120, 180, 240 and 300 minutes after the application of the gel and transdermal delivery patches. Blood glucose levels were determined at the same time points using glucose sticks (AccuChek, Roche Diagnostics).

Results

Figure 9:
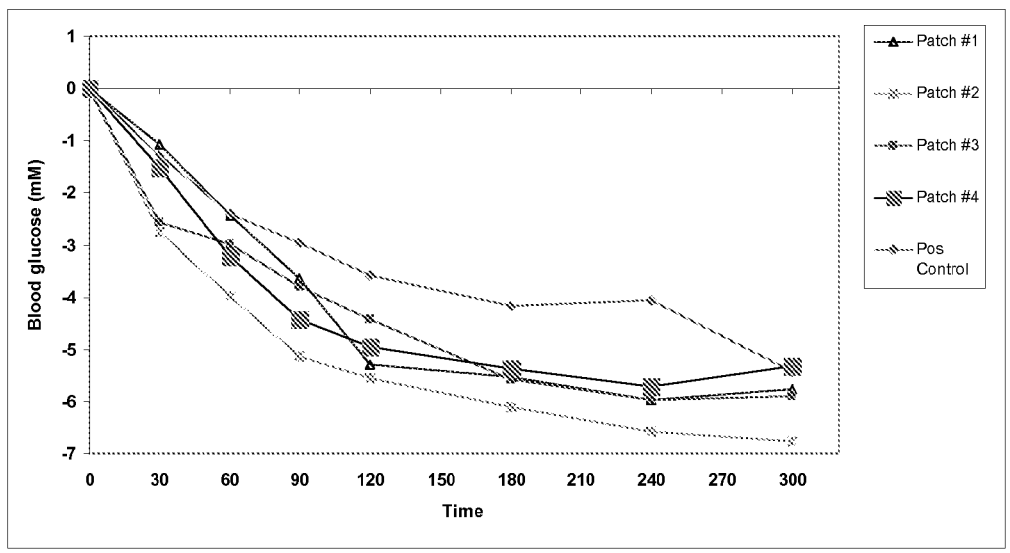
FIG. 9 is a graph showing the average change in blood glucose after application of transdermal delivery patches of the present invention to each of the animals.
Figure 10:
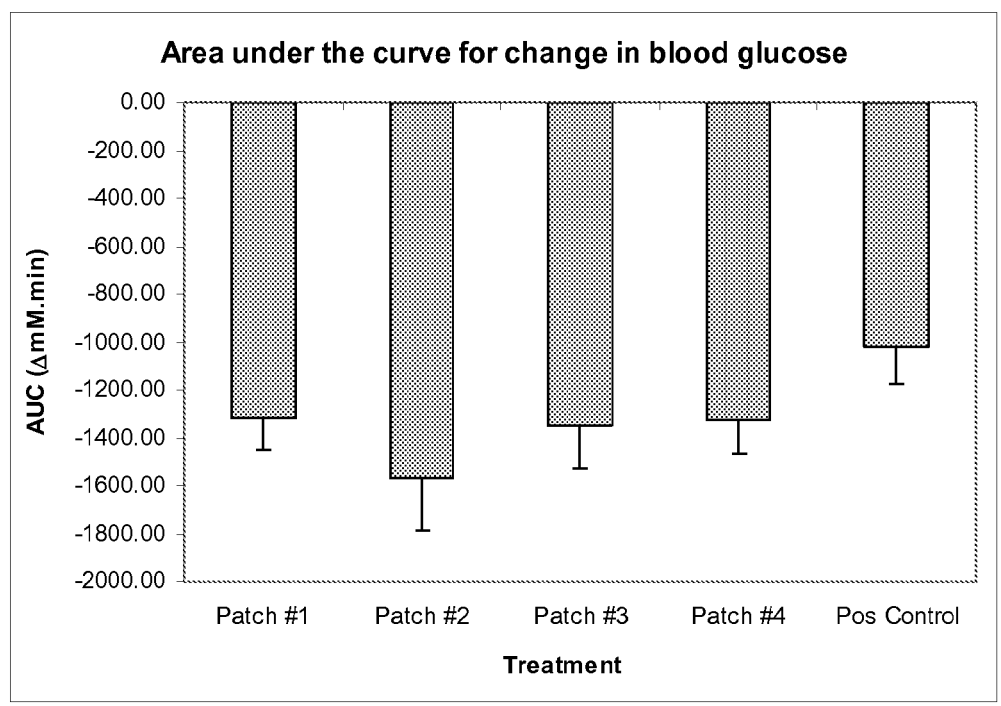
FIG. 10 is a graph showing the area under the curve of the graph of FIG. 9.

The gel and the transdermal delivery patches caused significant reductions in blood glucose concentrations in the diabetic rats (see FIGS. 9 and 10). Blood glucose was significantly reduced ($p<0.05$) from starting values 30 min after application and remained lowered for the duration of the experiment. There was no statistically significant difference in the reduction of blood glucose between the patches and gel tested here, as demonstrated by the area under the curve (see FIG. 10). The transdermal delivery patches appear efficacious for the delivery of insulin, however, a transdermal delivery patch provides the many advantages described herein over a gel or other methods of delivery.

Example 11

Diclofenac Transdermal Delivery Patch

Diclofenac diethylamine transdermal delivery patches were prepared having the following composition:

| |
|---|
| 200 mg diclofenac diethylamine |
| 20 mg TPM (8:2) |
| 168 mg Eudragit |
| 200 mg diclofenac diethylamine |
| 168 mg Eudragit |

The diclofenac diethylamine transdermal delivery patches had a surface area of 120 cm².

Manufacturing Method

The components listed in the table above were dissolved in 30 ml isopropanol:acetone mixture (1:1) at 45° C. The mixture was then casted over a 3M scotch pack, and dried for 90 minutes at 75° C.

In-Vitro Testing (Diffusion)

Transdermal delivery patches were cut into circular discs (7 cm²) and placed over rat skin. Receptor solution was 12 ml and had an effective surface with the skin equal to about 1.76 cm². After the duration of the experiment, skin (about 7 cm²) was removed, the surface cleaned (excess gel) and extracted with 10 ml solvent.

Results

Figure 11:
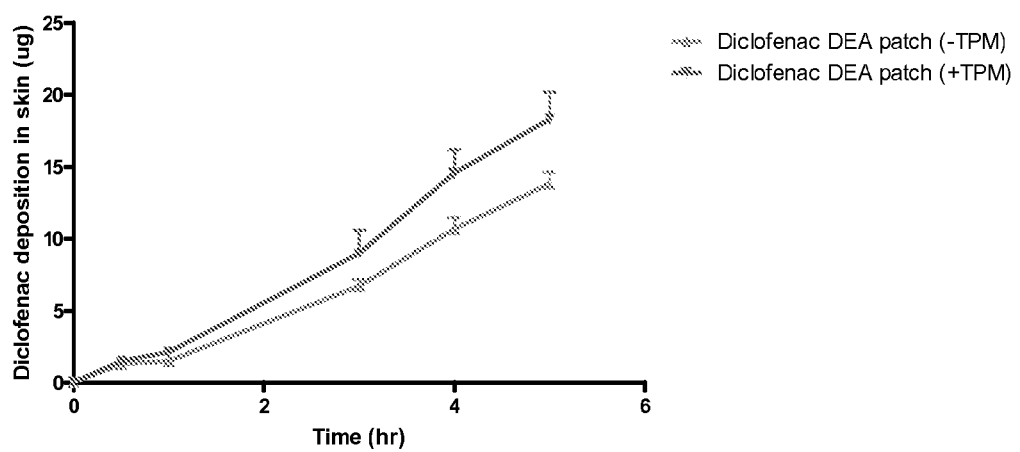
FIGS. 11 and 12 are graphs comparing the deposition in skin of two diclofenac transdermal delivery patches.
Figure 12:
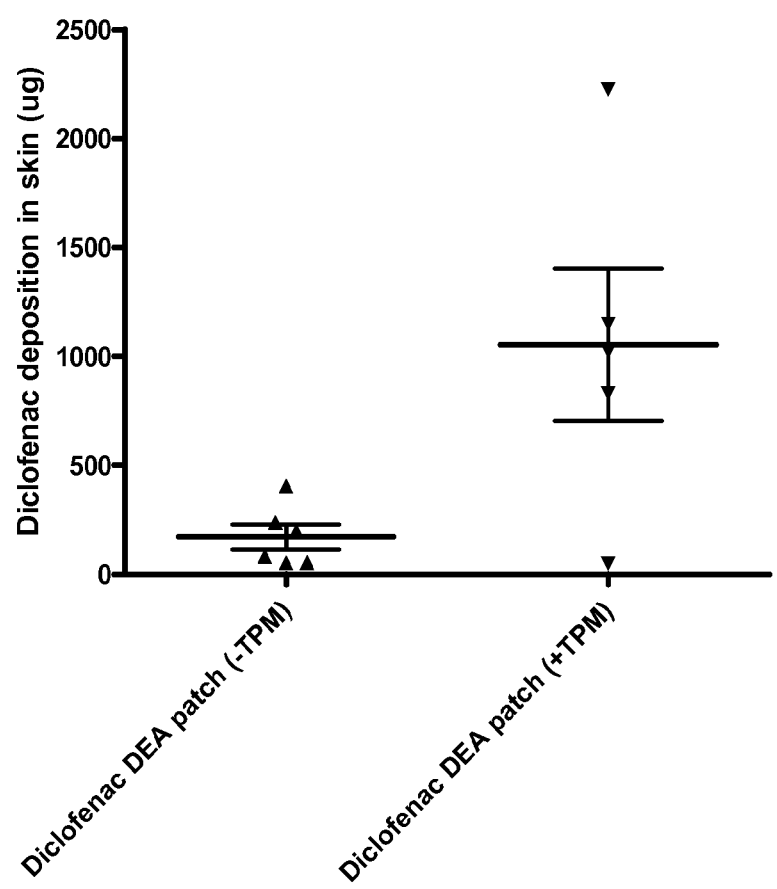

The results are reflected in FIGS. 11 and 12.

| | |
|---|---|
| Diffusion | Dose: 2.92 mg/1.76 cm² |
| Skin extraction | Dose: 11.78 mg/7.06 cm² |

Example 12

Lidocaine Transdermal Delivery Patches

Lidocaine transdermal delivery patches were prepared having the following composition:

| |
|---|
| 100 mg lidocaine base |
| 20 mg TPM (8:2) |
| 168 mg Eudragit |
| 100 mg lidocaine base |
| 168 mg Eudragit |

The lidocaine transdermal delivery patches had a surface area of 120 cm².

Manufacturing Method

The components listed in the table above were dissolved in 30 ml isopropanol:acetone mixture (1:1) at 45° C. The mixture was then casted over a 3M scotch pack, and dried for 90 minutes at 75° C.

In-Vitro Testing (Diffusion)

Transdermal delivery patches were cut into circular discs (7 cm²) and placed over rat skin. Receptor solution was 12 ml and had an effective surface with the skin equal to about 1.76 cm². After the duration of the experiment, skin (about 7 cm²) was removed, the surface cleaned (excess gel) and extracted with 10 ml solvent.

Results

Figure 13:
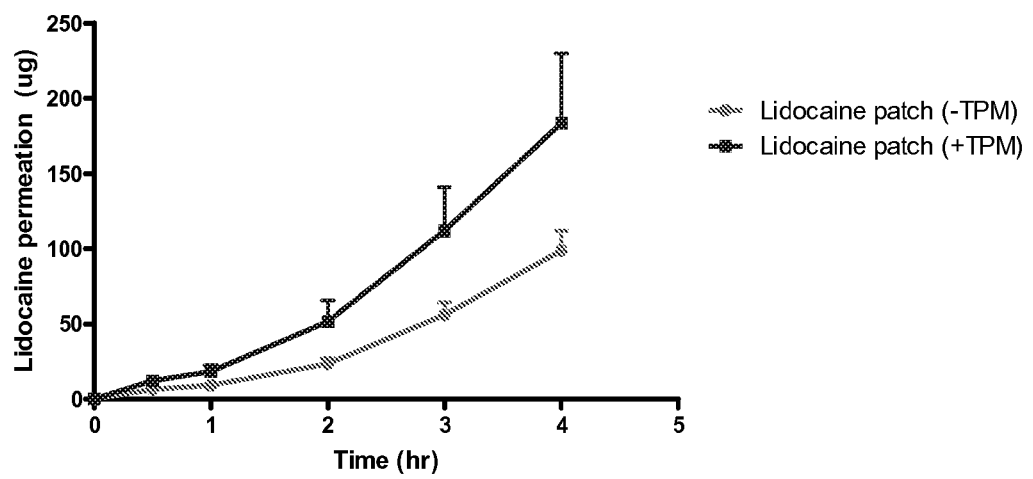
FIG. 13 is a graph comparing the permeation of two lidocaine transdermal delivery patches.

The results are reflected in FIG. 13.

| | |
|---|---|
| Diffusion | Dose: 1.46 mg/1.76 cm² |
| Skin extraction | Dose: 5.89 mg/7.06 cm² |

In this specification, except where the context requires otherwise, the words "comprise", "comprises", and "comprising" mean "include", "includes", and "including" respectively, i.e. when the invention is described or defined as comprising specified features, various embodiments of the same invention may also include additional features.

Although this invention has been described by example and with reference to possible embodiment thereof, it is to be understood that modifications or improvements may be made thereto without departing from the scope of the invention.

The invention claimed is:

1. A matrix layer suitable for use in a transdermal delivery patch for administration of a biologically active compound, the matrix layer comprising a mixture of a mono-tocopheryl phosphate compound and a di-tocopheryl phosphate compound and a polymer carrier comprising polymers selected from the group consisting of polyacrylates, rubber-based polymers, polysiloxanes and amine-resistant polysiloxanes, wherein the polymer carrier is present in an amount within the range of about 30% w/w to about 95% w/w of the total concentration of the matrix layer.

2. The matrix layer of claim 1, wherein the mono-tocopheryl phosphate compound is selected from the group consisting of mono-(tocopheryl)phosphate, mono-(tocopheryl) phosphate monosodium salt, mono-(tocopheryl)phosphate disodium salt, mono-(tocopheryl)phosphate monopotassium salt and mono-(tocopheryl)phosphate dipotassium salt, and the di-tocopheryl phosphate compound is selected from the group consisting of di-(tocopheryl)phosphate, di-(tocopheryl)phosphate monosodium salt and di-(tocopheryl)phosphate monopotassium salt.

3. The matrix layer of claim 1, wherein the ratio (% w/w) of the mixture of the mono-tocopheryl phosphate compound and the di-tocopheryl phosphate compound is at least 2:1.

4. The matrix layer of claim 1, wherein the mixture of the mono-tocopheryl phosphate compound and the di-tocopheryl phosphate compound is present in an amount within a range of about 0.01% w/w to about 10% w/w of the total concentration of the matrix layer.

5. The matrix layer of claim 1, wherein the mixture of the mono-tocopheryl phosphate compound and the di-tocopheryl phosphate compound is present in an amount within a range of about 0.5% w/w to about 1.5% w/w of the total concentration of the matrix layer.

6. The matrix layer of claim 1, wherein the polymer carrier is present in an amount within the range of about 30% w/w to about 80% w/w of the total weight of the matrix layer.

7. The matrix layer of claim 1, wherein the polymer carrier is present in an amount within the range of about 85% w/w to about 95% w/w of the total weight of the matrix layer.

8. The matrix layer of claim 1, wherein the polymer carrier further comprises inert carrier components selected from the group consisting of anti-tacking agents, tackifiers, and plasticizers.

9. The matrix layer of claim 8, wherein the anti-tacking agent is succinic acid.

10. The matrix layer of claim 8, wherein the anti-tacking agent is present in an amount of up to about 5% w/w of the total weight of the matrix layer.

11. The matrix layer of claim 8, wherein the tackifier is insoluble in water and composed of a monomer which contains partly or wholly a (meth)acrylic alkyl ester.

12. The matrix layer of claim 8, wherein the tackifier is selected from the group consisting of acrylic, N-butyl-methacrylic copolymer, acrylic methyl, acrylic 2-ethylhexyl copolymer, polyacrylic acid, methacrylic copolymer L, aminoalkylmethacrylate copolymer E, rosin esters, hydrogenated rosins, dipropylene glycol dibenzoate, mixed hydrocarbons, and acrylic copolymers.

13. The matrix layer of claim 8, wherein the plasticizer is selected from the group consisting of phthalates, esters of polycarboxylic acids with linear or branched aliphatic alcohols of moderate chain length, acetylated monoglycerides, alkyl citrates, triethyl citrate (TEC), acetyl triethyl citrate (ATEC), tributyl citrate (TBC), acetyl tributyl citrate (ATBC), trioctyl citrate (TOC), acetyl trioctyl citrate (ATOC), trihexyl citrate (THC), acetyl trihexyl citrate (ATHC), butyryl trihexyl citrate (BTHC, trihexyl o-butyryl citrate), trimethyl citrate (TMC), methyl laurate, lauric acid, lauryl lactate, lauryl alcohol, alkyl sulphonic acid phenyl ester, diethylene glycol monoethyl ether, bis(2-ethylhexyl) phthalate (DEHP), diisooctyl phthalate (DIOP), bis(n-butyl) phthalate (DnBP, DBP), diisobutyl phthalate (DIBP), bis(2-ethylhexyl)adipate (DEHA), dimethyl adipate (DMAD), monomethyl adipate (MMAD), dioctyl adipate (DOA), ethyl oleate, sorbitan monooleate, glycerol monooleate, dibutyl sebacate (DBS), dibutyl maleate (DBM), diisobutyl maleate (DIBM), benzoates, epoxidized vegetable oils, tris (tromethamine), N-ethyl toluene sulfonamide (o/p ETSA), N-(2-hydroxypropyl)benzene sulfonamide (HP BSA), N-(n-butyl)benzene sulfonamide (BBSA-NBBS), tricresyl phosphate (TCP), tributyl phosphate (TBP), triethylene glycol dihexanoate (3G6, 3 GH), tetraethylene glycol diheptanoate (4G7), 1,3-butyleneglycol, dipropylene glycol, PEG400, Span 80, and polyvinylpyrrolidone.

14. The matrix layer of claim 8, wherein the inert carrier components are present in an amount within the range of 0.001% w/w to about 50% w/w of the total weight of the matrix layer.

15. The matrix layer of claim 1, wherein the matrix layer comprises an anti-tacking agent and a plasticizer in a total amount of about 35% w/w of the total weight of the matrix layer.

16. The matrix layer of claim 15, wherein the anti-tacking agent is succinic acid and the plasticizer is dibutyl sebacate.

17. The matrix layer of claim 1, wherein the polymer carrier and optional inert carrier components is present in an amount within the range of about 50% w/w to about 99% w/w of the total weight of the matrix layer.

18. The matrix layer of claim 1, further comprising one or more excipients.

19. A transdermal delivery patch for administration of a biologically active compound comprising a matrix layer as defined in claim 1.

20. The transdermal delivery patch of claim 19, wherein the matrix layer is a solid or semi-solid layer.

21. The transdermal delivery patch of claim 19, further comprising one or more occlusive or impermeable layers, and/or one or more non-occlusive layers.

22. The transdermal delivery patch of claim 21, wherein an impermeable or occlusive layer is a backing layer.

23. The transdermal delivery patch of claim 21, wherein a non-occlusive layer is a backing layer.

24. The transdermal delivery patch of claim 22, wherein the thickness of the backing layer is about 0.0005 inches to about 0.01 inches.

25. The transdermal delivery patch of claim 21, wherein an impermeable layer is a removable release liner.

26. The transdermal delivery patch of claim 21, wherein the impermeable layers are made from metal foil, Mylar, polyethylene terephthalate, siliconized polyester, fumed silica in silicone rubber, polytretrafluoroethylene, cellophane, siliconized paper, aluminized paper, polyvinyl chloride film, composite foils or films containing polyester such as polyester terephthalate, polyester or aluminized polyester, polytetrafluoroethylene, polyether block amide copolymers, polyethylene methyl methacrylate block copolymers, polyurethanes, polyvinylidene chloride, nylon, silicone elastomers, rubber-based polyisobutylene, styrene, styrene-butadiene, and styrene-isoprene copolymers, polyethylene, polypropylene, or a combination thereof.

27. The transdermal delivery patch of claim 25, wherein the thickness of the release liner is about 0.01 mm to about 2 mm.

28. The transdermal delivery patch of claim 19, further comprising an adhesive layer.

29. The transdermal delivery patch of claim 28, wherein the adhesive layer is a polymeric adhesives selected from the group consisting of include polyacrylate polymers, rubber-based adhesives and polysiloxane adhesives; a commercially available adhesive selected from the group consisting of polyacrylate adhesives.

30. The transdermal delivery patch of claim 19, wherein the biologically active compound is selected from the group of pharmaceuticals including drugs, cosmeceuticals, nutraceuticals, and nutritional agents.

31. The transdermal delivery patch of claim 30, wherein the biologically active compound is selected from the group consisting of cardiovascular drugs, antihypertensive agents and antiarrhythmic agents; congestive heart-failure pharmaceuticals; inotropic agents; vasodilators; ACE inhibitors; diuretics; carbonic anhydrase inhibitors; cardiac glycosides; phosphodiesterase inhibitors; α blockers; β-blockers; sodium channel blockers; potassium channel blockers; β-adrenergic agonists; platelet inhibitors; angiotensin II antagonists; anticoagulants; thrombolytic agents; treatments for bleeding; treatments for anaemia; thrombin inhibitors; antiparasitic agents; antibacterial agents; insulin; human growth hormone and peptides; vaccines; antiinflammatory agents, steroidal antiinflammatory agents; prophylactic antiinflammatory agents; antiglaucoma agents; mast cell stabilisers; mydriatics; agents affecting the respiratory system; allergic rhinitis pharmaceuticals; alpha-adrenergic agonists; corticosteroids; chronic obstructive pulmonary disease pharmaceuticals; xanthine-oxidase inhibitors; antiarthritis agents; gout treatments; autacoids and autacoid antagonists; antimycobacterial agents; antifungal agents; antiprotozoal agents; anthelmintic agents; antiviral agents, herpes, cyto-megalovirus, human immunodeficiency virus and hepatitis infections; treatments for leukemia and kaposi's sarcoma; pain management agents, anaesthetics and analgesics; neuroleptics; sympathomimetic pharmaceuticals; adrenergic agonists; drugs affecting neurotransmitter uptake or release; anticholinergic pharmaceuticals; antihaemorrhoid treatments; agents to prevent or treat radiation or chemotherapeutic effects; liopgenisis drugs; fat reducing treatments; anti-obesity peptides; antiobesity agents; sympathomimetic agents; treatments for gastric ulcers and inflammation; prostaglandins; VEGF inhibitors; antihyperlipidemic agents, drugs that affect the central nervous system (CNS), psychoactive drugs, stimulants, antianxiety and hypnotic drugs, antidepressant drugs; antiparkinson's pharmaceuticals; hormones and fragments thereof; growth hormone antagonists; gonadotropin releasing hormones and analogues thereof; steroid hormones and their antagonists; selective estrogen modulators; growth factors; antidiabetic pharmaceuticals H1, H2, H3 and H4 antihistamines; peptide, protein, polypeptide, nucleic acids and oligonucleotide pharmaceuticals; analogues, fragments and varients of natural proteins, polypeptides, oligonucleotides and nucleic acids; agents used to treat migraine headaches; asthma pharmaceuticals; cholinergic antagonists; glucocorticoids; androgens; antiandrogens; inhibitors of adrenocorticoid biosynthesis; osteoporosis treatments; antithyroid pharmaceuticals; suncreens, sun protectants and filters; cytokine agonists; cytokine antagonists; anticancer drugs; antialzheimer drugs; HMGCoA reductase inhibitors; fibrates; cholesterol absorption inhibitors; HDL cholesterol elevating agents; triglyceride reducing agents; antiageing or antiwrinkle agents; precursor molecules for the generation of hormones; proteins; antibacterial agents; anti acne agents; antioxidants; hair treatments and skin whitening agents; suncreens, sun protectants and filters; variants of human apolipoprotein; precursor molecules for generation of hormones; proteins and peptides thereof; amino acids; plant extracts; DHEA; isoflavones; nutritional agents, phytosterols and iridoid gylcosides, sesquiterpene lactones, terpenes, phenolic glycosides, triterpenes, hydroquinone derivatives, phenylalkanones; antioxidants; omega-3-fatty acids; glucosamine; nucleic acids, oligonucleotides, antisense pharmaceuticals; enzymes; cytokines; cytokine analogues; cytokine agonists; cytokine antagonists; immunoglobulins; antibodies; antibody pharmaceuticals; gene therapies; lipoproteins; erythropoietin; vaccines; small and large molecule therapeutic agents for the treatment, of human and animal diseases.

32. The transdermal delivery patch of claim 31, wherein the biologically active compound is selected from the group consisting of alprazolam, donepazil, rispiredone, lorazepam, nicotine, lidocaine, diclofenac, felodipine, insulin, ketoralac, prilocalne, halobetasol, hydrocortisol, opioids, oxycodone, and dihydrohydroxycodeinone.

33. The transdermal delivery patch of claim 19, wherein the biologically active compound is present in an amount of the total concentration of the matrix layer.

34. The transdermal delivery patch of claim 33, wherein the amount of biologically active compound is present in an amount within the range of about 3.0% w/w to about 15.0% w/w of the total concentration of the matrix layer.

35. The transdermal delivery patch of claim 19, wherein the ratio (% w/w) of biologically active compound:tocopheryl phosphate mixture is within the range of about 5:5 to about 5:0.5.

36. The transdermal delivery patch of claim 19, wherein the ratio (% w/w) of polymer carrier:biologically active compound and tocopheryl phosphate mixture is within the range of about 1:1 to about 3:1.

37. The matrix layer of claim 1, wherein the polymer carrier is present in an amount within the range of about 55% w/w to about 65% w/w of the total weight of the matrix layer.

38. The matrix layer of claim 1, wherein the polymer carrier is present in an amount within the range of about 90% w/w to about 95% w/w of the total weight of the matrix layer.

39. The transdermal delivery patch of claim 31, wherein the biologically active compound is selected from the group consisting of calcium channel blockers, calcium antagonists, non-steroidal anti-inflammatory agents (NSAIDs), COX-2 inhibitors, lipase inhibitors, proton pump inhibitors, statins, antipsychotic drugs, antiepileptic drugs, antiseizure drugs, anticonvulsants, sex hormones, hypoglycaemic agents, bisphosphonates, collagen, elastin, grape seed extract, vitamins, retinol, retinoids, retinoic acid and co-enzyme Q10.

40. The transdermal delivery patch of claim 19, wherein the biologically active compound is present in an amount within the range of about 0.1% w/w to about 20% w/w of the total concentration of the matrix layer.

41. The transdermal delivery patch of claim 19, wherein the biologically active compound is present in an amount within the range of about 0.1% w/w to about 10% w/w of the total concentration of the matrix layer.

42. The transdermal delivery patch of claim 19, wherein the ratio (% w/w) of the biologically active compound:tocopherol phosphate mixture is within the range of about 5:1.

43. The transdermal delivery patch of claim 19, wherein the ratio (% w/w) of polymer carrier:biologically active compound and tocopherol phosphate mixture is within the range of about 7:6 to about 7:3.

44. The transdermal delivery patch of claim 32, wherein the oxycodone is oxycodone base.

* * * * *